(12) United States Patent  
Kozlowski

(10) Patent No.: US 8,076,412 B2
(45) Date of Patent: *Dec. 13, 2011

(54) WATER-SOLUBLE POLYMER ALKANALS

(75) Inventor: Antoni Kozlowski, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/908,266

(22) Filed: Oct. 20, 2010

(65) Prior Publication Data

US 2011/0034737 A1  Feb. 10, 2011

Related U.S. Application Data

(63) Continuation of application No. 12/361,427, filed on Jan. 28, 2009, now Pat. No. 7,838,595, which is a continuation of application No. 11/375,698, filed on Mar. 13, 2006, now Pat. No. 7,511,094, which is a continuation of application No. 10/659,734, filed on Sep. 9, 2003, now Pat. No. 7,157,546.

(60) Provisional application No. 60/456,580, filed on Mar. 19, 2003, provisional application No. 60/409,251, filed on Sep. 9, 2002.

(51) Int. Cl.
C08G 63/48 (2006.01)
C08G 63/91 (2006.01)
C08G 10/00 (2006.01)
C08G 12/00 (2006.01)

(52) U.S. Cl. ...... 525/50; 525/54.1; 525/54.11; 525/54.2; 525/54.3; 528/288; 528/310; 528/332; 530/300; 530/334; 568/497

(58) Field of Classification Search ............. 525/50, 525/54.1, 54.2, 54.3, 54.11; 528/230, 491; 530/391.9, 406; 568/497
See application file for complete search history.

(56) References Cited

U.S. PATENT DOCUMENTS

| 4,002,531 A | 1/1977 | Royer |
| 5,037,969 A | 8/1991 | Minami et al. |
| 5,252,714 A | 10/1993 | Harris et al. |
| 5,510,418 A | 4/1996 | Rhee et al. |

(Continued)

FOREIGN PATENT DOCUMENTS

EP  0 372 752 A2  5/1993

(Continued)

OTHER PUBLICATIONS

Aoki, et al., "Reversible Alignment Change of Liquid Crystals Induced by Photochromic Molecular Films; 15 a) Convenient Methods to Prepare "Command Surfaces" by Surface-Selective Modification of Thin Films of Poly(vinyl alcohol) with Azobenzene Units", Makromol. Chem., vol. 193, No. 8, pp. 2163-2174 (1992).

(Continued)

*Primary Examiner* — Duc Truong

(74) *Attorney, Agent, or Firm* — Susan T. Evans; Mark A. Wilson

(57) ABSTRACT

The present invention is directed to alkanal derivatives of water-soluble polymers such as poly(ethylene glycol), their corresponding hydrates and acetals, and to methods for preparing and using such polymer alkanals. The polymer alkanals of the invention are prepared in high purity and exhibit storage stability.

28 Claims, 1 Drawing Sheet

U.S. PATENT DOCUMENTS

| | | | |
|---|---|---|---|
| 5,672,662 | A | 9/1997 | Harris et al. |
| 5,824,784 | A | 10/1998 | Kinstler et al. |
| 5,840,900 | A | 11/1998 | Greenwald et al. |
| 5,962,447 | A | 10/1999 | Rogers et al. |
| 5,990,237 | A | 11/1999 | Bentley et al. |
| 6,465,694 | B1 | 10/2002 | Baudys et al. |
| 6,495,659 | B2 | 12/2002 | Bentley et al. |
| 6,916,962 | B2 | 7/2005 | Rosen et al. |
| 6,956,135 | B2 | 10/2005 | Rosen et al. |
| 7,157,546 | B2 | 1/2007 | Kozlowski |
| 7,273,909 | B2 | 9/2007 | Won |
| 7,511,094 | B2 * | 3/2009 | Kozlowski ............. 525/50 |
| 7,838,592 | B2 | 11/2010 | Kozlowski |
| 7,838,595 | B2 * | 11/2010 | Kozlowski ............. 525/50 |
| 2003/0171285 | A1 | 9/2003 | Finn et al. |
| 2004/0127417 | A1 | 7/2004 | Finn |
| 2004/0142870 | A1 | 7/2004 | Finn |

FOREIGN PATENT DOCUMENTS

| | | |
|---|---|---|
| JP | 56-095142 A | 8/1981 |
| JP | 06-233816 A | 8/1994 |
| JP | 11-322916 A | 11/1999 |
| JP | 2000-303090 A | 10/2000 |
| WO | WO 96/08716 A1 | 3/1996 |
| WO | WO 98/41562 A1 | 9/1998 |
| WO | WO 00/32772 A2 | 6/2000 |
| WO | WO 02/059179 A2 | 8/2002 |
| WO | WO 03/040211 A2 | 5/2003 |
| WO | WO 03/044056 A2 | 5/2003 |
| WO | WO 03/049699 A2 | 6/2003 |
| WO | WO 03/061577 A2 | 7/2003 |
| WO | WO2004/013205 A1 | 2/2004 |

OTHER PUBLICATIONS

Chamow, et al., "Modification of CD4 Immunoadhesin with Monomethoxypoly(ethylene glycol) Aldehyde via Reductive Alkylation", Bioconjugate Chem., vol. 5, pp. 133-140 (1994).

The International Search Report for PCT Patent Application No. PCT/US2003/028221, Search Report dated Feb. 19, 2004, 4 pages (2004).

The International Preliminary Examination Report for PCT Patent Application No. PCT/US2003/028221, report completion dated, Dec. 3, 2004, 4 pages (2004).

Harris, et al., "New Polyethylene Glycols for Biomedical Applications", Water-Soluble Polymers Synthesis, Solution Properties, and Applications, ACS Symposium Series, vol. 467, pp. 418-429 (1991).

Harris, et al.; "Poly(ethylene glycols) as Soluble, Recoverable, Phase-Trasfer Catalysts", Journal of Organic Chemistry, vol. 47, pp. 4789-4791 (1982).

Harris, et al., "Synthesis and Characterization of Poly(ethylene Glycol) Derivatives", J. of Polymer Sci.: Polymer Chem. Ed., vol. 22, pp. 341-352 (1984).

Japanese Office Action in Japanese Patent Application No. 2004-534787 mailed on Jul. 2, 2009.

Marko, et al., "Copper-Catalyzed Oxidation of Alcohols to Aldehydes and Ketones: An Efficient, Aerobic Alternative", Science, vol. 274, pp. 2044-2046 (1996).

Nektar Advanced PEGylation Catalog, "Polyethylene Glycol and Derivatives for Advanced PEGylation," pp. 1-21 (2003).

NOF Corporation Catalog, "Peg Derivatives, Phospholipid and Drug Delivery Materials for Pharmaceuticals," No. 1, pp. 1-46 (2003).

Paley, et al., "Synthesis of the Aldehyde of Oligomeric Polyoxyethylene," J. of Polymer Sci.: Part A: *Polymer Chem.*, vol. 25, pp. 2447-2454 (1987).

Shearwater Polymers, Inc., Catalog, , "Functionalized Biocompatible Polymers for Research Polyethylene Glycol and Derivatives," pp. 2-49 (Mar. 1995).

Shearwater Polymers, Inc., Catalog, "Functionalized Biocompatible Polymers for Research and Pharmaceuticals: Polyethylene Glycol and Derivatives," pp. 2-53 (1997-1998).

Shearwater Polymers, Inc., Catalog, "Functionalized Biocompatible Polymers for Research and Pharmaceuticals: Polyethylene Glycol and Derivatives," pp. 2-50 (2000).

Shearwater Corporation Catalog, "Polyethylene Glycol and Derivatives for Biomedical Applications," pp. 1-17 (2001).

Topchiyeva, "Synthesis of Biologically Active Polyethylene Glycol Derivatives. A Review," Polymer Sci. U.S.S.R., vol. 32, No. 5, pp. 833-851 (1990).

Vandoorne, et al., "Functionalization of α-hydrogen-ω-methoxypoly(oxyethylene),1: A new method for the conversion of hydroxyl end groups into aldehyde groups," Makromol. Chem., Rapid Commun., vol. 10, pp. 271-275 (1989).

Enzon Pharmaceuticals Catalog, "Macromolecular Engineering Technologies," pp. 1-14 (2004).

Nektar Advanced PEGylation Catalog, "Polyethylene Glycol and Derivatives for Advanced PEGylation," pp. 1-24 (2004).

Nektar Advanced PEGylation Catalog, "Polyethylene Glycol and Derivatives for Advanced PEGylation," pp. 1-30 (2005-2006).

NOF Corporation Catalog, "Peg Derivatives, Phospholipid and Drug Delivery Materials for Pharmaceuticals," No. 2, pp. 2-50 (2003).

NOF Corporation catalog, "Peg Derivatives, Phospholipid and Drug Delivery Materials for Pharmaceuticals/Products and Formulations", pp. 1-59 (2006).

NOF Corporation website, "PEGylation and Activated PEGs", retrieved from the NOF Corporation website on Dec. 12, 2006, 9 pages (2006).

Polypure Products Catalog, 5 pages (Apr. 2004).

Polypure Products catalog, 5 pages (Apr. 2005).

Quanta Biodesign Catalog, pp. 1-38 (Mar. 12, 2004).

Quanta Biodesign Catalog, pp. 1-31 (Nov. 5, 2004).

Quanta Biodesign Limited Catalog, pp. 1-51 (Jul. 18, 2005).

Quanta Biodesign Limited catalog. pp. 1-51 (Nov. 17, 2005).

* cited by examiner

WATER-SOLUBLE POLYMER ALKANALS

CROSS REFERENCE TO RELATED APPLICATIONS

This application is a Continuation of U.S. patent application Ser. No. 12/361,427, now U.S. Pat. No. 7,838,595, filed Jan. 28, 2009, which is a Continuation of U.S. patent application Ser. No. 11/375,698, now U.S. Pat. No. 7,511,094, filed Mar. 13, 2006, which is a Continuation of U.S. patent application Ser. No. 10/659,734, filed Sep. 9, 2003 now U.S. Pat. No. 7,157,546, which claims the benefit of priority to Provisional Patent Application No. 60/409,251, filed Sep. 9, 2002, and to Provisional Patent Application No. 60/456,580, filed Mar. 19, 2003, each of which is incorporated herein by reference in its entirety.

FIELD

This disclosure relates to particular aldehyde derivatives of water-soluble polymers, and to methods for preparing and using such polymer aldehyde derivatives.

BACKGROUND

In recent years, human therapeutics have expanded past traditional small molecule drugs and into the realm of biopharmaceuticals. The discovery of novel proteins and peptides has led to the development of numerous protein and polypeptide biopharmaceuticals. Unfortunately, proteins and polypeptides, when utilized as therapeutics, often exhibit properties that make them extremely difficult to formulate or administer, such as short circulating half lives, immunogenicity, proteolytic degradation, and low solubility. One approach for improving the pharmacokinetic or pharmacodynamic properties of biopharmaceuticals is the conjugation to natural or synthetic polymers, such as polyethylene glycol (PEG). The covalent attachment of PEG to a therapeutic protein can provide a number of advantages, such as (i) shielding antigenic epitopes of the protein, thus reducing its reticuloendothelial clearance and recognition by the immune system, (ii) reducing degradation by proteolytic enzymes, and (iii) reducing renal filtration.

Much effort has been spent on the development of polymer derivatives for coupling to biopharmaceuticals such as peptides, and in particular, on the development of polymer derivatives for coupling to reactive amino groups of proteins. Such polymer derivatives are referred to as 'electrophilically activated', since they bear electrophilic groups suitable for reaction with nucleophiles such as amines. Examples of such PEG derivatives include PEG dichlorotriazine, PEG tresylate, PEG succinimidyl carbonate, PEG carbonylimidazole, and PEG succinimidyl succinate. Unfortunately, use of these particular reagents can result in one or more of the following: undesirable side reactions under the reaction conditions necessary to effect coupling, lack of selectivity, and/or the formation of weak (i.e., unstable) linkages between the biopharmaceutical and the PEG.

In an effort to overcome some of these problems, many new or "second generation" electrophilically activated PEGs have been developed, such as PEG propionaldehyde and PEG acetaldehyde (see, for Example, U.S. Pat. Nos. 5,252,714 and 5,990,237, respectively). Aldehyde derivatives are particularly attractive reagents for coupling to proteins and other biomolecules, since aldehydes react only with amines (i.e., are selective in their attachment chemistry). The above-mentioned reagents offer many advantages: they can be prepared to avoid the problems of PEG diol contamination, are not restricted to low molecular weight mPEG, form stable amine linkages upon coupling, and are selective. Although the above noted derivatives offer many advantages over first-generation PEG reagents, the Applicants have noted some particular drawbacks of these aldehyde reagents, making them less than ideal in certain instances.

More specifically, the Applicants have recognized, in their extensive work with these reagents, that PEG acetaldehyde is very unstable, particularly in basic media, and is difficult to isolate due to excessive salt formation resulting from neutralization of the reaction mixture. In particular, PEG acetaldehyde is very susceptible to dimerization via aldol condensation. PEG propionaldehyde, while a much better reagent in terms of its stability, possesses some disadvantages due to side reactions that can occur during its preparation, making it difficult to obtain the PEG propionaldehyde product in high purity.

More specifically, the Applicants have found that when preparing PEG propionaldehyde in situ from its precursor PEG aldyhyde hydrate, product yields are generally only about 50%, due to an elimination reaction that consumes a significant portion of the acetal reagent. Although an improved synthetic route for the synthesis of PEG propionaldehyde can be employed, i.e., via base-catalyzed reaction of 3-hydroxypropionaldehyde diethyl acetal with PEG mesylate, the Applicants have discovered that this reaction route also leads to an elimination side reaction that produces significant amounts of PEG vinyl ether, which is unstable and produces difficult-to-remove the parent dihydroxy PEG (also referred to as PEG diol). Consequently, the yield of this reaction is generally less than about 85 to 90%. Moreover, using either of the above-described PEG propionaldehyde syntheses requires hydrolysis of the acetal intermediate at very low pHs, e.g., at pHs of 2 or lower. Hydrolysis at such low pHs is undesirable due to the large amounts of base necessary to neutralize the reaction mixture to pHs suitable for conjugation. Additionally, coupling PEG propionaldehyde to a protein at basic pHs can be problematic due to formation of significant amounts of acrolein (resulting from a retro-Michael type side reaction), which is quite difficult to remove. Formation of such undesirable side products necessitates extensive purification to obtain a pharmaceutical grade product.

Thus, there exists a need for improved electrophilically activated polymer derivatives for conjugating to biologically active molecules and surfaces, particularly polymer derivatives that (i) are selective in their coupling chemistry, (ii) can be prepared in high yields and in few reaction steps, (iii) are stable over a wide range of pHs, (iv) can be readily isolated, (iv) can be prepared in high purity (i.e., substantially absent polymer-derived impurities and side-products, and (v) overcome at least some of the drawbacks of known polymer derivatives such as those described above.

SUMMARY

The present invention provides a unique family of polymer alkanals—i.e., polymers comprising at least one aldehyde functionality coupled to a polymer segment by one or more interposing carbon atoms.

The polymer alkanals of the invention are, for the most part, less reactive than prior art aldehyde derivatives and, thus, more selective. Further, the polymer alkanals of the invention are prepared in high yield, and certain structures can be prepared in a straightforward one step process. Certain of the polymer aldehydes described herein are more stable at basic pHs than prior known aldehyde derivatives, and are formed without significant or even detectable amounts of retro-Michael type reaction side products. Moreover, the polymer alkanals of the invention are formed from the corresponding acetal precursors by hydrolysis under mild acidic conditions, i.e., under much less harsh acidic conditions than required for either PEG acetaldehyde or PEG propionaldehyde. Such mild conditions allow direct in situ conjugation of the polymer derivatives of the invention with proteins, peptides, or other molecular targets without requiring an intervening isolation step. The polymer alkanals of the invention are also prepared in high purity, making them particularly advantageous for coupling to drugs and biopharmaceuticals to provide polymer conjugate compositions having a purity sufficient for administration to a mammalian subject.

More particularly, in one aspect, the present invention is directed to a water-soluble polymer having the structure:

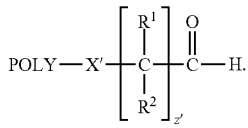

I

In the above structure, POLY represents a water-soluble polymer segment; X' is a linker moiety; z' is an integer from 1 to about 21; $R^1$, in each occurrence, is independently H or an organic radical selected from the group consisting of alkyl, substituted alkyl, alkenyl, substituted alkenyl, alkynyl, substituted alkynyl, aryl, and substituted aryl; and $R^2$, in each occurrence, is independently H or an organic radical selected from the group consisting of alkyl, substituted alkyl, alkenyl, substituted alkenyl, alkynyl, substituted alkynyl, aryl, and substituted aryl.

In some instances, the polymer alkanals of the invention will possess certain features. For example, according to one embodiment of the invention, when POLY is linear: (a) the total number of carbonyls (excluding/not counting the aldehyde carbonyl carbon) present in the polymer is 0 or 2 or greater except when X' comprises one or more contiguous (—$CH_2CH_2O$—) or (—$CH_2CH_2NH$—) segments. When X' comprises one or more contiguous (—$CH_2CH_2O$—) or (—$CH_2CH_2NH$—) segments, then the total number of carbonyls present in the polymer is 0, 1, 2, or greater.

In yet another example, according to a further embodiment, when X' is oxygen or comprises at least one (—$CH_2CH_2O$—) segment and z' is from 2 to 12, then at least one of $R^1$ or $R^2$ in at least one occurrence is an organic radical as defined above or the polymer is heterobifunctional, where POLY comprises a reactive group at one terminus that is not hydroxyl.

The polymer alkanals provided herein may possess any of a number of overall geometries or structures, to be described in greater detail herein. Preferably, when POLY is branched, then either (i) at least one of $R^1$ or $R^2$ in at least one occurrence is an organic radical as defined above or (ii) X' includes —($CH_2CH_2O$)$_b$— where b is from 1 to about 20 in the instance where POLY comprises a lysine residue. Alternatively, when POLY is branched and possesses two polymer arms, then neither polymer arm comprises oxygen as the only heteroatom in the instance where POLY comprises "C—H" as a branch point.

Generally speaking, the polymer alkanals of the invention possess a structure where z' falls within one of the following ranges: z' is from about 2 to 21, from about 3 to 12, from about 3 to 8, or from 3 to about 6.

In one particular embodiment of the invention, the polymer has the structure:

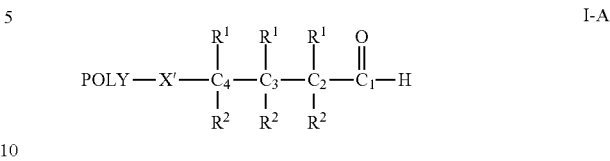

I-A where POLY, X', each $R^1$, each $R^2$ and $R^3$ are as defined above. In the preceding structure, $C_1$ indicates the aldehyde carbonyl carbon; $C_2$ indicates the carbon adjacent to or α (alpha) to the carbonyl carbon or $C_1$; $C_3$ indicates the carbon atom once removed from the carbonyl carbon or in the β (beta) position; and C4 indicates the carbon atom in the γ position. Polymer alkanals having the overall structure depicted by I-A are generally referred to herein as polymer butanals. In preferred variations of formula I-A above, $R^1$ attached to $C_2$ is alkyl, and all other $R^1$ and $R^2$ variables are H. Preferably, the $R^1$ attached to $C_2$ is lower alkyl. Alternatively, the polymer alkanal corresponds to structure I-A above, where the $R^1$ attached to $C_3$ is alkyl, and all other $R^1$ and $R^2$ variables are H. In yet another preferred embodiment, the polymer alkanal is described by structure I-A where the $R^1$ attached to $C_4$ is alkyl, and all other $R^1$ and $R^2$ variables are H.

In yet another particular embodiment, a polymer alkanal of the invention corresponds to formula I, and possesses an additional carbon atom in the alkylene chain when compared to structure I-A. In this embodiment (see structure I-B herein), z' is 4, the $R^1$ attached to $C_2$ is alkyl, and all other $R^1$ and $R^2$ variables are H. Alternatively, either the $R^1$ attached to $C_3$ or $C_4$ is alkyl, and all other $R^1$ and $R^2$ variables are H.

In yet another particular embodiment falling within formula I, z' is 5, the $R^1$ attached to $C_2$ is alkyl, and all other $R^1$ and $R^2$ variables are H (see structure I-C herein). Alternatively, one of the $R^1$ variables attached to $C_3$ or $C_4$ or $C_5$ is alkyl, and all other $R^1$ and $R^2$ variables are H.

The polymer alkanal in accordance with formula I, in certain embodiments, possesses a linker moiety described generally by the formula: —$(CH_2)_c$-$D_e$-$(CH_2)_f$— or —$(CH_2)_p$-$M_r$—C(O)—$K_s$—$(CH_2)_q$—, where c ranges from zero to 8; D is O, NH, or S; e is 0 or 1; f ranges from zero to 8; p ranges from zero to 8; M is —NH or O; K is NH or O; q ranges from zero to 8, and r and s are each independently 0 or 1. Specific linkers falling within this general formula are described in greater detail below.

The linker moiety may optionally include an oligomeric segment corresponding to the structure —($CH_2CH_2O$)$_b$— or —($CH_2CH_2NH$)$_g$—, where b and g are each independently 1 to 20. Preferably, b and g each independently range from about 1 to 10, and even more preferably range from about 1 to about 6. These oligomeric linkers provide additional stability to the alkanals of the invention, and also provide advantages in the synthetic methodology for preparing the polymers, to be described in more detail below.

More particularly, in certain embodiments, X' comprises a moiety corresponding to the structure: —$(CH_2)_c$-$D_e$-$(CH_2)_f$—P— or —$(CH_2)_p$-$M_r$-C(O)—$K_s$—$(CH_2)_q$-T-, where P and T are each independently —($CH_2CH_2O$)$_b$— or —($CH_2CH_2NH$)$_g$; and b and g each independently range from 1 to about 20. In a specific embodiment of a polymer alkanal in accordance with formula I, X' comprises —C(O)NH—$(CH_2)_{1-6}$NH—C(O)— or —NHC(O)NH—$(CH_2)_{1-6}$NH—C(O)—.

Preferably, the water-soluble polymer segment of a polymer alkanal of the invention is a poly(alkylene oxide), a poly(vinyl pyrrolidone), a poly(vinyl alcohol), a polyoxazoline, a poly(acryloylmorpholine), or a poly(oxyethylated polyol). In a preferred embodiment, the polymer segment is a poly(alkylene oxide), preferably poly(ethylene glycol).

According to one embodiment, the poly(ethylene glycol) segment comprises the structure: Z—(CH$_2$CH$_2$O)$_n$— or Z—(CH$_2$CH$_2$O)$_n$—CH$_2$CH$_2$—, where n ranges from about 10 to about 4000 and Z is, a moiety comprising a functional group selected from the group consisting of hydroxy, amino, ester, carbonate, aldehyde, alkenyl, acrylate, methacrylate, acrylamide, sulfone, thiol, carboxylic acid, isocyanate, isothiocyanate, hydrazide, maleimide, vinylsulfone, dithiopyridine, vinylpyridine, iodoacetamide, alkoxy, benzyloxy, silane, lipid, phospholipid, biotin, and fluorescein.

Alternatively, POLY may be terminally capped with an end-capping moiety such as alkoxy, substituted alkoxy, alkenyloxy, substituted alkenyloxy, alkynyloxy, substituted alkynyloxy, aryloxy, and substituted aryloxy. Preferred end-capping groups include methoxy, ethoxy, and benzyloxy.

Generally, POLY possesses a nominal average molecular mass falling within one of the following ranges: from about 100 daltons to about 100,000 daltons, from about 1,000 daltons to about 50,000 daltons, or from about 2,000 daltons to about 30,000 daltons. Preferred molecular masses for POLY include 250 daltons, 500 daltons, 750 daltons, 1 kDa, 2 kDa, 5 kDa, 10 kDa, 15 kDa, 20 kDa, 30 kDa, 40 kDa, and 50 kDa, or even greater.

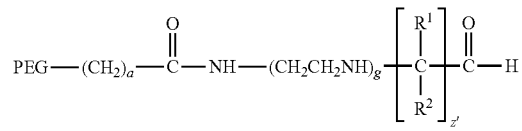

IV-A

In the above structures, PEG is poly(ethylene glycol), and b and g are each independently 0 to 20, a is 0 to 6. For generalized structures provided in this section, variables correspond to ranges/values previously provided unless otherwise noted.

In a specific embodiment, a polymer alkanal in accordance with the invention corresponds to the structure:

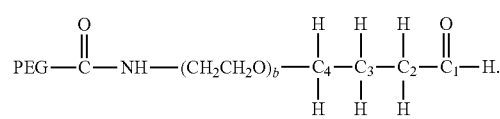

III-D

One particularly preferred polymer alkanal falling within the generalized structure III-D possesses the structure:

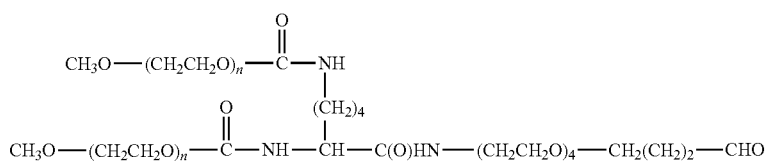

III-E

In yet another particular embodiment, the polymer alkanal of the invention comprises the structure:

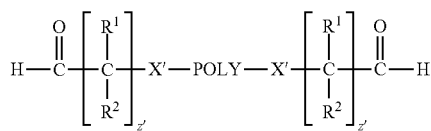

II wherein POLY, each X', each (z'), each R$^1$, each R$^2$, and each R$^3$ are as previously defined. In a specific embodiment, POLY is linear and the polymer is homobifunctional.

As stated above, the polymer segment within the polymer alkanal may possess any of a number of geometries, such as linear, branched, forked, multi-armed, or dendritic, to be described in greater detail below.

Specific embodiments of the invention include polymer alkanals corresponding to the following structures:

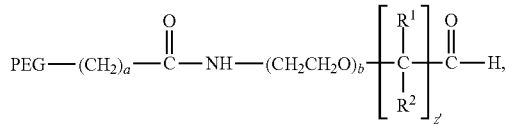

III-A

According to another aspect, the invention is directed to a composition comprising a water-soluble polymer having the structure:

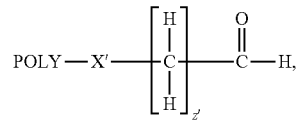

VII where the composition is absent detectable amounts of iodine-containing species or retro-Michael type reaction products. This is particularly advantageous, since iodine-containing species can lead to degradation of poly(ethylene glycol) chains due to chain cleavage, resulting in a polymer product having a high polydispersity value, e.g., greater than around 1.2. Preferably, a polymer alkanal of the invention will possess a polydispersity value of less than about 1.2, preferably less than about 1.1, and even more preferably less than about 1.05. Even more preferred are polymer alkanals such as those described herein characterized by a polydispersity of 1.04, 1.03 or less.

In accordance with yet another aspect, the invention relates to a composition comprising a water-soluble polymer having the structure:

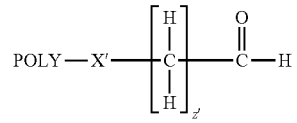

where POLY is a linear, terminally end-capped water-soluble polymer segment and the composition is absent detectable amounts of dialdehyde polymer derivative.

One additional feature of the polymer alkanals of the invention is their stability, e.g., storage stability, in comparison to other known polymer aldehyde compositions. For example, provided herein is a polymer alkanal composition that exhibits 10% or less degradation of the polymer aldehyde group when stored at 40° C. for 15 days, as determined by NMR.

In a preferred embodiment, the composition of the invention comprises a polymer alkanal corresponding to the following structure:

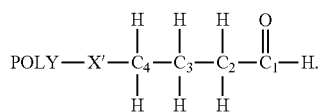

VII-A

In an even more preferred embodiment, in accordance with structure VII-A, POLY possesses the structure $Z—(CH_2CH_2O)_n—CH_2CH_2—$, where X is O, n ranges from about 10 to about 4000, and Z comprises a functional group, targeting moiety, reporter, capping group, or the like.

Another composition of the invention comprises a polymer in accordance with the structure:

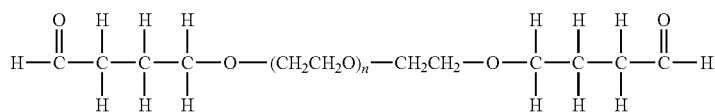

VIII

In yet another aspect of the invention, provided are hydrate or acetal forms of the above-described polymer alkanals.

Acetals of the invention include dimethyl acetal, diethyl acetal, di-isopropyl acetal, dibenzyl acetal, 2,2,2-trichloroethyl acetal, bis(2-nitrobenzyl)acetal, S,S'-dimethyl acetal, S,S'-diethyl acetal, and dioxolanes.

More particularly, an acetal or hydrate form of a polymer alkanal of the invention may be described generally by the following structure:

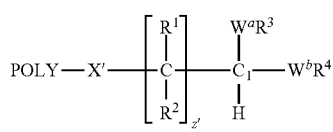

IX where $W^a$ and $W^b$ are each independently O or S, and $R^3$ and $R^4$ are each independently H, or an organic radical selected from the group consisting of methyl, ethyl, isopropyl, benzyl, 1,1,1-trichoroethyl, and nitrobenzyl, or when taken together, are $—(CH_2)_2—$ or $—(CH_3)_3—$, forming a 5 or 6 membered ring when considered together with $W^a$, $C_1$, and $W^b$. The polymer acetals are useful precursors of the alkanals of the invention, and can be hydrolyzed to yield a polymer alkanal.

In one particular embodiment, provided is a water-soluble polymer having the structure:

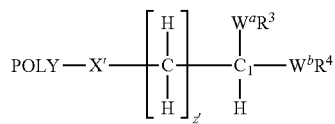

IX-A

In structure IX-A, the alkanal is one having only methylene or $—(CH_2)—$ carbons separating the acetal or aldehyde hydrate portion of the molecule from the linker, X'.

Further, the invention is directed to conjugates formed by reaction of a biologically active agent with the herein described polymer alkanals, their hydrates and/or the corresponding alkanals.

Preferably, the conjugate corresponds to the following structure:

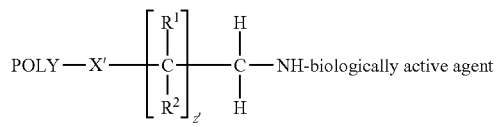

where "NH-biologically active agent" represents a biologically active agent comprising an amino group.

Also forming part of the present invention are hydrogels formed from the herein described polymer alkanals or their precursors.

In accordance with yet another aspect, the invention provides protected aldehydes reagents. These protected aldehyde reagents are particularly useful for forming the polymer alkanals of the invention, and correspond generally to the following structures:

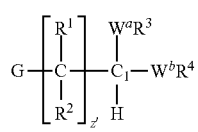

XI-A

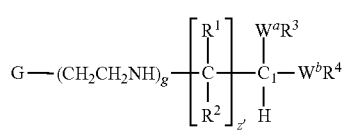

XI-B

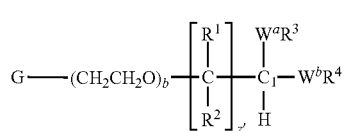

XI-C where G is a functional group, and the remaining variables have the values set forth above.

In preferred embodiments of structures XI-A, B, and C, G is a leaving group such as chloride, bromide, para-tolylsulfonate ester, methylsulfonyl ester, trifluorosulfonylester, and trifluoroethylsulfonyl ester.

Alternatively, G is a functional group selected from the group consisting of —OH, —NH$_2$, —SH, and protected forms thereof.

Another aspect of the invention is directed to a method for preparing a water-soluble polymer alkanal, optionally in protected form. Briefly, the method includes the steps of reacting a water soluble polymer comprising at least one reactive group, Y, with a protected alkanal reagent comprising from about 2 to 20 carbon atoms and a reactive group, K, suitable for displacement by or alternatively, reaction with Y, under conditions effective to form a water soluble polymer alkanal in protected form. In this method, an activated polymer is coupled to a reagent bearing the alkanal portion of the final product, or a precursor thereto.

Preferably, the reaction is carried out under an inert atmosphere.

In one specific embodiment, POLY-Y, is prepared by direct polymerization.

The method may also include the additional step of hydrolyzing the protected water soluble polymer alkanal, e.g., under acidic conditions, to form the corresponding water soluble polymer alkanal.

In a preferred embodiment, the hydrolyzing step is carried out at a pH of no lower than about 3.

Protected forms of the alkanal reagent for carrying out the method include acetals such as dimethyl acetal, diethyl acetal, di-isopropyl acetal, dibenzyl acetal, 2,2,2-trichloroethyl acetal, bis(2-nitrobenzyl)acetal, S,S'-dimethyl acetal, and S,S'-diethyl acetal, cyclic acetals and cyclic thioacetals.

In yet a further embodiment, the polymer alkanal thus produced is recovered by raising the pH of the reaction mixture to from about 6.0 to 7.5, extracting the polymer alkanal into an organic solvent, and removing the solvent.

In a preferred embodiment of the method, the water soluble polymer corresponds to the structure, "POLY-Y", and the protected alkanal reagent corresponds to the structure:

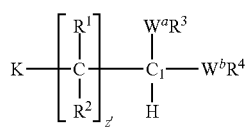

XI-D

Preferably, POLY comprises a poly(ethylene glycol) that may or may not be terminally end-capped.

In one particular embodiment of the method, POLY-Y comprises the structure Z—(CH$_2$CH$_2$O)$_n$H, wherein n is from about 10 to about 4000, and Z is selected from the group consisting of —OCH$_3$, —OCH$_2$CH$_3$, and —OCH$_2$(C$_6$H$_5$). In a further embodiment, POLY-Y comprises the structure Z—(CH$_2$CH$_2$O)$_n$CH$_2$CH$_2$O$^-$M$^+$, where POLY-Y is prepared by anionic ring-opening polymerization of ethylene oxide onto an end-capped alcoholate salt such as Z—CH$_2$CH$_2$O$^-$M$^+$, prepared by metallation of the terminal —OH group of Z—CH$_2$CH$_2$OH with a strong base. M$^+$ represents a metal counterion such as Na$^+$, K$^+$, Li$^+$, Cs$^+$, Rb$^+$. POLY-Y thus prepared is then suitable for reaction with a protected alkanal reagent as described above.

In yet a further particularly preferred embodiment, the recovered alkanal is absent detectable amounts of unreacted POLY Y (e.g., Z—(CH$_2$CH$_2$O)$_n$H) and retro-Michael type reaction products.

In yet another embodiment of the method, POLY-Y corresponds to PEG-diol, that is to say, POLY-Y possesses the structure HO—(CH$_2$CH$_2$O)$_n$H, wherein n is from about 10 to about 4000, K is selected from the group consisting of:

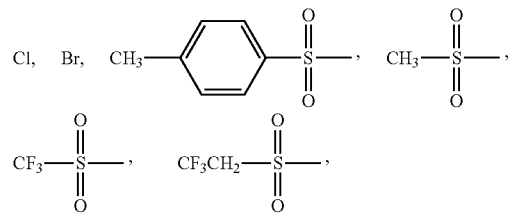

the method results in formation of a protected polymer alkanal having the structure:

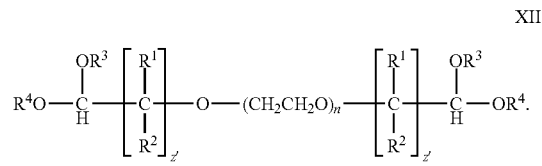

XII

In yet another embodiment of the method, POLY-Y comprises the structure Z—(CH$_2$CH$_2$O)$_n$H, wherein n is from about 10 to about 4000, and Z is protected hydroxyl. In this instance, a preferred embodiment of the method includes deprotecting the protected hydroxyl after the reacting step, optionally followed by converting the terminal hydroxyl of the poly(ethylene glycol) to a functional group other than hydroxyl.

Exemplary functional groups include amino, ester, carbonate, aldehyde, alkenyl, acrylate, methacrylate, acrylamide, sulfone, thiol, carboxylic acid, isocyanate, isothiocyanate, maleimide, vinylsulfone, dithiopyridine, vinylpyridine, iodoacetamide, and silane. Preferably, the functional group is selected from the group consisting of N-hydroxysuccinimidyl ester, benzotriazolyl carbonate, amine, protected amine, vinylsulfone, and maleimide.

In accordance with yet another embodiment of the invention, "Y" in POLY-Y is an ionizable group or is a derivative of an ionizable group such as a carboxylic acid, active ester, or amine. Preferably, POLY-Y has been chromatographically purified prior to use in the reacting step. In one particular embodiment, POLY-Y is purified prior to use by ion exchange chromatography. Ideally, such chromatographically purified POLY-Y for use in the reacting step is essentially absent detectable amounts of polymeric impurities. In one such embodiment of this method, POLY-Y is end-capped, and is essentially absent detectable amounts of PEG-diol or difunctional PEG impurities.

Alternatively, in practicing the method of the invention, the alkanal reagent comprises the structure:

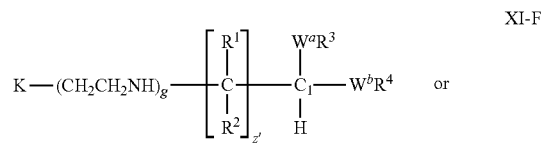

XI-F

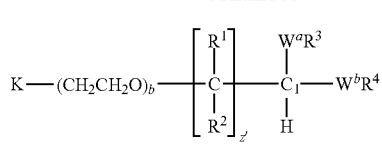

XI-G where g and b each independently range from about 1 to about 20. As an example, a preferred alkanal reagent corresponds to the structure:

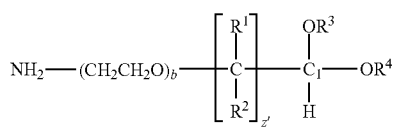

XI-H and the product of the reacting step possesses the generalized structure:

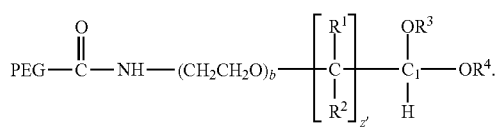

IX-B

In yet another approach for preparing a polymer alkanal of the invention, a polymer alkanal as described herein is prepared by building the polymer segment directly onto an acetal precursor, e.g., by direct polymerization. More specifically, this method comprises the steps of:

(i) providing an acetal precursor comprising at least one active anionic site suitable for initiating polymerization, (ii) contacting the anionic site of the acetal precursor with a reactive monomer capable of polymerizing, to thereby initiate polymerization of the reactive monomer onto the acetal precursor, (iii) as a result of said contacting step, adding additional reactive monomers to the acetal precursor to form a polymer chain, (iv) allowing said contacting to continue until a desired length of the polymer chain is reached, and (v) terminating the reaction to achieve a polymer aldehyde precursor of the invention.

The resulting polymer aldehyde precursor can be further hydrolyzed to the corresponding alkanal as set forth above, if desired.

In one particular embodiment of the above method, the reactive monomer is ethylene oxide and the reactive anionic site contained within the acetal precursor is an alkoxide anion (O—), preferably accompanied by an alkali metal or other suitable counterion. The alkoxide end group present in the acetal precursor is active for anionic ring opening polymerization of ethylene oxide to form a polymer alkanal of the invention.

The acetal precursor will generally possess a structure corresponding to:

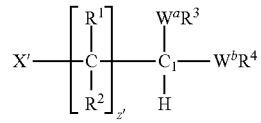

where the variables possess the values described above, with the exception that X' terminates in an oxygen anion, or O⁻ (e.g., in its neutral form, X' typically terminates in a hydroxyl group or —OH, that in the presence of a strong base, is converted to the corresponding alkoxide salt). Suitable counterions include $Na^+$, $K^+$, $Li^+$, and $Cs^+$. The terminating step generally comprises neutralizing the reaction, e.g., by addition of acid. Optionally, the polymer segment may be capped by addition of an alkylating reagent or other reagent suitable for providing a non-reactive terminus.

These and other objects and features of the invention will become more fully apparent when read in conjunction with the following detailed description.

DETAILED DESCRIPTION

Figure 1:
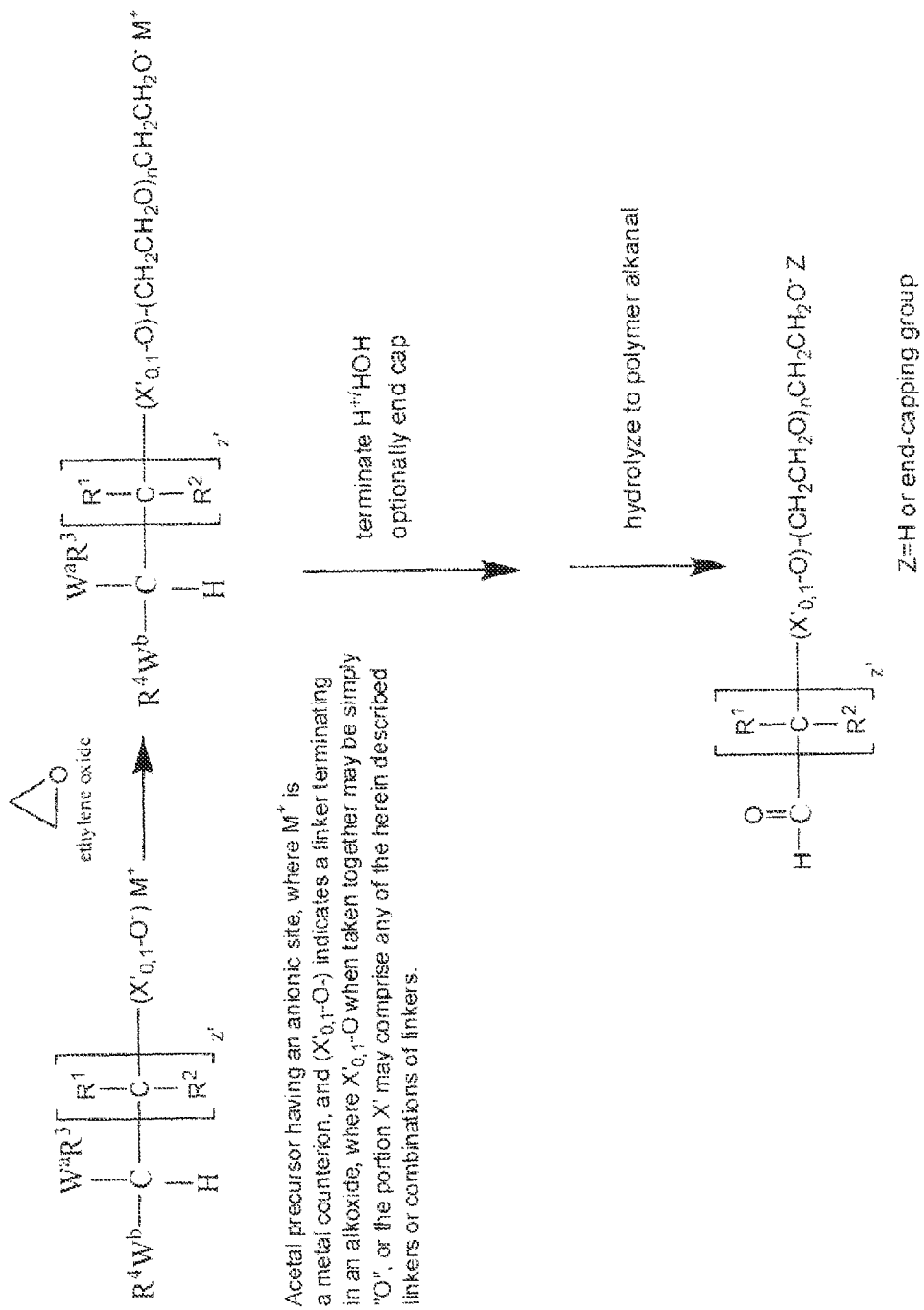
FIG. 1 is a general reaction scheme for preparing a polymer alkanal of the invention by anionic ring opening polymerization of ethylene oxide (EO) on an acetal precursor having an anionic site.

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

Definitions

The following terms as used herein have the meanings indicated.

As used in the specification, and in the appended claims, the singular forms "a", "an", "the", include plural referents unless the context clearly dictates otherwise.

"PEG" or "poly(ethylene glycol)" as used herein, is meant to encompass any water-soluble poly(ethylene oxide). Typically, PEGs for use in the present invention will comprise one of the two following structures: "—(CH₂CH₂O)ₙ—" or "—(CH₂CH₂O)ₙ₋₁CH₂CH₂—," depending upon whether or not the terminal oxygen(s) has been displaced, e.g., during a synthetic transformation. The variable (n) is 3 to 3000, and the terminal groups and architecture of the overall PEG may vary. When PEG further comprises a linker moiety (to be described in greater detail below), the atoms comprising the linker (X'), when covalently attached to a PEG segment, do not result in formation of (i) an oxygen-oxygen bond (—O—O—, a peroxide linkage), or (ii) a nitrogen-oxygen bond (N—O, O—N). "PEG" means a polymer that contains a majority, that is to say, greater than 50%, of subunits that are —$CH_2CH_2O$—. PEGs for use in the invention include PEGs having a variety of molecular weights, structures or geometries (e.g., branched, linear, forked PEGs, dendritic, and the like), to be described in greater detail below.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. For instance, an end capped PEG will typically comprise the structure "RO—(CH2CH2O)n-", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like.

"Non-naturally occurring" with respect to a polymer of the invention means a polymer that in its entirety is not found in nature. A non-naturally occurring polymer of the invention may however contain one or more subunits or segments of subunits that are naturally occurring, so long as the overall polymer structure is not found in nature.

"Molecular mass" in the context of a water-soluble polymer of the invention such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of less than about 1.20.

The term "reactive" or "activated" when used in conjunction with a particular functional group, refers to a functional group that reacts readily with an electrophile or a nucleophile, typically present on another molecule, to undergo a transformation. This is in contrast to those groups that require strong catalysts or harsh reaction conditions in order to react (i.e., a "nonreactive" or "inert" group).

The term "protected" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., PROTECTIVE GROUPS IN ORGANIC SYNTHESIS, 3rd ed., John Wiley & Sons, Inc., New York, N.Y. (1999).

As used herein, the term "functional group" or any synonym thereof is meant to encompass protected forms thereof.

The term "linker moiety" is used herein to refer to an atom or a collection of atoms optionally used to link interconnecting moieties, such as a polymer segment and an alkanal. The linker moieties of the invention may be hydrolytically stable or may include a physiologically hydrolyzable or enzymatically degradable linkage.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Alkanal" refers to the aldehyde portion of a water soluble polymer of the invention (CHO), including the carbonyl carbon and any additional methylenes or substituted methylenes (—$C(R^1)(R^2)$— up to the linker moiety connecting the alkanal portion of the polymer to the polymer segment. In naming an alkanal segment, C1 corresponds to the carbonyl carbon. The term "alkanal" as used herein is meant to encompass hydrate and protected forms of the aldehyde group, as well as chalcogen analogs. One particularly preferred protected form of an alkanal of the invention is an acetal.

"Total number of carbonyls", in reference to certain polymer alkanals of the invention, is the total number of carbonyl groups contained in the polymer alkanal, not counting the aldehyde carbon(s).

"Branched" in reference to the geometry or overall structure of a polymer refers to polymer having 2 or more polymer "arms". A branched polymer may possess 2 polymer arms, 3 polymer arms, 4 polymer arms, 6 polymer arms, 8 polymer arms or more. One particular type of highly branched polymer is a dendritic polymer or dendrimer, that for the purposes of the invention, is considered to possess a structure distinct from that of a branched polymer.

"Branch point" refers to a bifurcation point comprising one or more atoms at which a polymer splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

A "retro-Michael type product" refers to a product arising from the reverse of a Michael-type addition reaction. A Michael addition reaction (forward direction) refers to the addition of a nucleophilic carbon species to an electrophilic double bond. Typically, but not necessarily, the nucleophile is an enolate or an enamine although the nucleophile can also be an alkoxide or an amine or other species. The electrophile is typically an alpha, beta-unsaturated ketone, ester, or nitrile, although other electron-withdrawing groups can also activate a carbon-carbon double bond to nucleophilic attack A product arising from the reverse (or backwards direction) of a Michael-type addition as described above, that is to say, an elimination reaction resulting in the loss of a nucleophilic carbon species (that may be but is not necessarily an enolate or enamine) and formation of an electrophilic double bond such as an alpha, beta unsaturated ketone or the like as described above is considered a retro-Michael type product. For example, a retro-Michael-type reaction of mPEG-propionaldehyde results in the retro-Michael type products, mPEG-OH and acrolein ($CH_2=CH—CHO$).

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer backbone having 3 or more functional groups contained therein, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "difunctional" polymer means a polymer having two functional groups contained therein, typically at the polymer termini. When the functional groups are the same, the polymer is said to be homodifunctional. When the functional groups are different, the polymer is said to be heterobifunctional A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

As used herein, "hydrate" refers to a hydrated aldehyde resulting from addition of a water molecule to the aldehyde group, which replaces the carbonyl functionality with two hydroxyl groups. Aldehydes reach equilibrium with the corresponding hydrate n water.

The term "chalcogen analog" refers to aldehyde analogs wherein the oxygen atom is replaced with another heteroatom, generally sulfur, selenium, or tellurium.

The term "patient," refers to a living organism suffering from or prone to a condition that can be prevented or treated by administration of a polymer of the invention, typically but not necessarily in the form of a polymer-active agent conjugate, and includes both humans and animals.

"Optional" or "optionally" means that the subsequently described circumstance may or may not occur, so that the description includes instances where the circumstance occurs and instances where it does not.

The Polymer

In a first aspect, the invention provides a water-soluble polymer having a reactive aldehyde group. The polymers of the invention are unique in many respects. They are prepared not only in high yield, but are also storage stable due to the absence of deleterious reaction side-products that can lead to polymer chain degradation and poor polymer polydispersity. The polymers, in particular end-capped polymers, are additionally prepared in high purity, e.g., absent detectable amounts of PEG-diol derived and other polymeric impurities. This feature is particularly advantageous for preparing high molecular weight end-capped PEG polymers, e.g., having a molecular weight of about 30 kDa or greater, where the amount of PEG diol impurity in raw material such as mPEG can range from about 2% by weight to 30% by weight or greater, depending upon the supplier. Moreover, in certain embodiments, the polymers of the invention are less reactive than other known polymer aldehydes, making them more discriminatory in conjugation reactions and more stable during transformation, handling, and reaction work-up.

General Structural Features and Alkanal Portion

Generally speaking, the polymer of the invention possesses a polymer segment connected to from about 1 to about 21 contiguous methylenes or substituted methylenes terminating in an aldehyde function (i.e., the alkanal portion) via an interposing linker moiety. A generalized structure corresponding to the polymer of the invention is provided below as Structure I.

Structure I

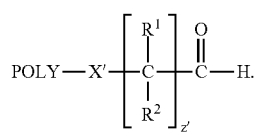

In reference to the description above when viewed in conjunction with structure I, the polymer segment is represented by POLY, the linker moiety is represented by X', and the contiguous methylenes (forming an alkylene chain) or substituted methylenes (forming a substituted alkylene chain) are represented by $—C(R^1)(R^2)—$. More specifically, in Structure I, POLY is a water-soluble polymer segment; X' is a linker moiety; and z' is an integer from 1 to about 21. $R^1$, in each occurrence, is independently H or an organic radical such as alkyl, substituted alkyl, alkenyl, substituted alkenyl, alkynyl, substituted alkynyl, aryl, and substituted aryl. $R^2$, in each occurrence, is also independently H or an organic radical such as from the group consisting of alkyl, substituted alkyl, alkenyl, substituted alkenyl, alkynyl, substituted alkynyl, aryl, and substituted aryl. Although many of the structures explicitly provided herein are aldehydes, it is to be understood that these same structures and indeed the invention as a whole is meant to extend to the corresponding aldehyde hydrates, aldehydes in protected form, and chalcogen analogues. where the carbonyl oxygen in structure I is replaced by a sulfur, selenium, or tellurium.

The present invention provides considerable flexibility with regard to the size of the alkylene chain connected to the aldehyde group. The carbon chain length is considered as the carbonyl carbon (C1) plus the number of intervening carbon atoms, (e.g., the total number of Cs comprising the $[—C(R^1)(R^2)]z'$ portion of the polymer), connecting the carbonyl carbon to the linker. The carbon chain length is typically 3 to about 22 carbon atoms, or more typically from about 4 to about 13 carbon atoms. In reference to structure I above, this means that the value of z' typically ranges from 2 to about 21, or more typically from about 3 to 12. More explicitly, the value of z' is most typically one of the following: 1, 2, 3, 4, 5, 6, 7, 8, 9, 10, 11, 12, or greater. Most preferred are z' values in the range from 2 to about 8. One particularly preferred polymer alkanal of the invention is one where z' is 3.

In referring to structure I above, certain types of alkanals are particularly preferred. Such compounds include alkanals as described above having at least one organic radical positioned on at least one "C" in the carbon chain. The organic radical may be any of the organic radicals mentioned above, e.g., alkyl, substituted alkyl, alkenyl, substituted alkenyl, alkynyl, substituted alkynyl, aryl, and substituted aryl, with alkyl being preferred. Typically, the alkyl group is straight chain lower alkyl or branched lower alkyl such as methyl, ethyl, propyl, isopropyl, n-butyl, isobutyl, sec-butyl, pentyl, etc., with straight chain being generally preferred. One particularly preferred alkyl substituent is methyl.

Although the alkanal portion of the polymer may possess more than one organic radical positioned on one or more "C"s in the carbon chain, one type of preferred alkanal is one in which only one "C" in the carbon chain is substituted with an organic radical and all other $R^1$ and $R^2$ are H. For example, regardless of the length of the alkylene chain, preferred are alkanals where all the $R^1$ and $R^2$ variables are H, with the exception that: (i) one of $R^1$ or $R^2$ positioned at C-2 is alkyl, or (ii) one of $R^1$ or $R^2$ positioned at C-3 is alkyl; or (iii) one of $R^1$ or $R^2$ positioned at C-4 is alkyl; or (iv) one of $R^1$ or $R^2$ positioned at C-5 is alkyl, and so on. One particularly preferred type of substituent in this regard is lower alkyl such as methyl, ethyl, or propyl. The synthesis of an illustrative 2-methyl substituted alkanal of the invention, mPEG-2-methylbutyraldehyde, is described in Example 17.

In focusing at present on the alkanal portion of the polymer, certain preferred alkanals are shown below.

Structure I-A

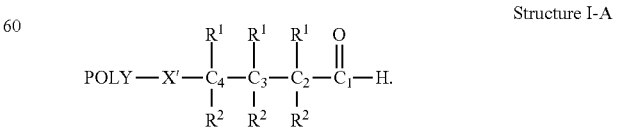

Structure I-A is one where the value of z' from structure I is 3. This structure, regardless of whether any one or more of C2, C3, or C4 is substituted with an alkyl or other organic radical as described above, is referred to herein as a "butyraldehyde" or as a "butanal". Illustrative polymer butyraldehyde of the invention include those where the alkanal portion of the polymer is 2-methylbutyraldehyde, 3-methylbutyraldehyde, or 4-methylbutyraldehyde, 2-ethylbutyraldehyde, 3-ethylbutyraldehyde, or 4-ethylbutyraldehyde.

Structure I-B

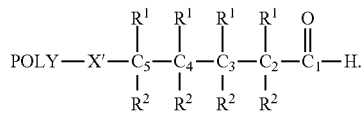

Structure I-B is one where the value of z' from structure I is 4. This structure, regardless of whether any one or more of C2, C3, C4, or C5 is substituted with an alkyl or other organic radical as described above, is referred to herein as a "pentanal" or as a "valeraldehyde". Illustrative polymer pentanals of the invention include those where the alkanal portion of the polymer is 2-methylpentanal, 3-methylpentanal, 4-methylpentanal, or 5-methylpentanal. Additional polymer pentanals include those where the alkanal portion of the polymer is 2-ethylpentanal, 3-ethylpentanal, 4-ethylpentanal, or 5-ethylpentanal.

Structure I-C

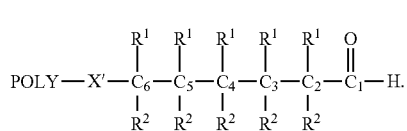

Structure I-C is one where the value of z' in structure I is 5. This structure, regardless of whether any one or more of C2, C3, C4, C5 or C6 is substituted with an alkyl or other organic radical as described above, is referred to herein as a "hexanal". Illustrative polymer hexanals of the invention include those where the alkanal portion of the polymer is 2-methylhexanal, 3-methylhexanal, 4-methylhexanal, 5-methylhexanal, 6-methylhexanal, 2-ethylpentanal, 3-ethylpentanal, 4-ethylpentanal, or 5-ethylpentanal.

Additional alkanal components of a polymer of the invention include heptanals, octanals, nonanals, and the like.

The Linker Moiety

In turning now to the linker moiety, a linker moiety or simply "linker" of the invention is represented generally by the variable, X'. The linker moiety is the portion of the overall polymer that links the alkanal portion of the polymer with the polymer segment (to be described in greater detail below). A linker of the invention may be a single atom, such as an oxygen or a sulfur, two atoms, or a number of atoms. A linker is typically but is not necessarily linear in nature. The overall length of the linker will typically range between 1 to about 40 atoms, where by length is meant the number of atoms in a single chain, not counting substituents. For instance, —$CH_2$— counts as one atom with respect to overall linker length, —$CH_2CH_2O$— counts as 3 atoms in length. Preferably, a linker will have a length of about 1 to about 20 atoms, or from about 2 to about 15 atoms.

A linker of the invention can be a single functional group such as an amide, an ester, a urethane, or a urea, or may contain methylene or other alkylene groups flanking either side of the single functional group. Alternatively, a linker may contain a combination of functional groups that can be the same or different. Additionally, a linker of the invention can be an alkylene chain, optionally containing one or more oxygen or sulfur atoms (i.e., an ether or thioether). Preferred linkers are those that are hydrolytically stable. When viewed in the context of structure I, a linker is one that when considered as part of the overall polymer, does not result in an overall structure containing a peroxide bond (—O—O—) or an —N—O— or —O—N— bond.

Illustrative linkers, X', are those corresponding to either of the following structures:

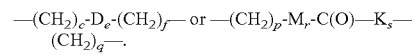

In referring to the linker structures above, the variable "c" ranges from zero to 8; "D" is O, NH, or S; the variable "e" is 0 or 1; the variable "f" ranges from zero to 8; the variable "p" ranges from zero to 8; "M" is —NH or O; "K" is NH or O; the variable "q" ranges from zero to 8, and the variables "r" and "s" are each independently 0 or 1.

In the context of structure I, a linker of the invention, X', may be any of the following: —O—, —NH—, —S—, —C(O)—, C(O)—NH, NH—C(O)—NH, O-C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$H_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH-$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—$CH_2$—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—, —$CH_2$—$CH_2$—C(O)—NH—$CH_2$—$CH_2$—NH—, —$CH_2$—$CH_2$—C(O)—NH—$CH_2$—$CH_2$—NH—C(O)—, —$CH_2$—$CH_2$—C(O)—NH—$CH_2$—$CH_2$—NH—C(O)—$CH_2$—, bivalent cycloalkyl group, —N($R^6$)—, —$CH_2$—$CH_2$—C(O)—NH—$CH_2$—$CH_2$—NH—C(O)—$CH_2$—$CH_2$—, —O—C(O)—NH—[$CH_2$]$_h$—(O$CH_2CH_2$)$_j$—, and combinations of two or more of any of the foregoing, wherein (h) is 0 to 6, (j) is 0 to 20, $R^6$ is H or an organic radical selected from the group consisting of alkyl, substituted alkyl, alkenyl, substituted alkenyl, alkynyl, substituted alkynyl, aryl and substituted aryl. Other specific linkers have the structures: —C(O)NH—($CH_2$)$_{1-6}$NH—C(O)—, or —NHC(O)NH—($CH_2$)$_{1-6}$NH—C(O)— or —OC(O) NH—($CH_2$)$_{1-6}$NH—C(O)—, where the subscript values following each methylene indicate the possible number of methylenes contained in the linker structure, e.g., $(CH_2)_{1-6}$ means that the linker may contain 1, 2, 3, 4, 5, or 6 methylenes.

For purposes of the present disclosure, however, a series of atoms is not considered as a linker moiety when the series of atoms is immediately adjacent to a polymer segment, POLY, and the series of atoms is but another monomer such that the proposed linker moiety would represent a mere extension of the polymer chain. For example, given the partial structure "POLY-X'-," where POLY in this instance is defined as "$CH_3O(CH_2CH_2O)_n$—", the linker moiety would not be "—$CH_2CH_2O$—" since such a definition would merely represent an extension of the polymer. That is not to say, however, that a linker of the invention cannot possess one or more contiguous —$CH_2CH_2O$— portions. For example, a linker may contain one or more (—$CH_2CH_2O$—) subunits flanked on one or both sides by one or a combination of illustrative linkers as provided above.

That is to say, a linker as described above can also include an oligomer such as —$(CH_2CH_2O)_b$— or —$(CH_2CH_2NH)_g$—, where b and g each independently range from 1 to about 20. The applicants have found that the inclusion of such oligomers within the linker can lend stability to the ultimate polymer alkanal product by extending the distance between the aldehyde functionality and any reactive groups contained within the linker. In this way, intramolecular interactions are disfavored, leading to increased yields during preparation and improved stability of the polymer alkanal product. Preferably, the variables b and g range from about 1 to 10, or in certain instances, range between about 1 to 6. The synthesis of an illustrative polymer alkanal having four contiguous —$(CH_2CH_2O)$— units in the linker is described in Example 5.

Additional examples of specific linkers containing —$(CH_2CH_2O)_b$— or —$(CH_2CH_2NH)_g$— oligomeric segments are shown below, where X' includes or is defined by the following:

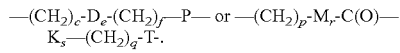

In the illustrative structures above, P and T are each independently —$(CH_2CH_2O)_b$— or —$(CH_2CH_2NH)_g$, b and g are each independently 1 to 20, and the remaining variables are as defined above. Examples of preferred linkers of this sort are —O—C(O)—NH—$(CH_2CH_2O)_b$—, —C(O)—NH—$(CH_2CH_2O)_b$—, —NH—C(O)—NH—$(CH_2CH_2O)_b$—, —O—C(O)—NH—$(CH_2CH_2NH)_g$—, —C(O)—NH—$(CH_2CH_2NH)_g$—, and —NH—C(O)—NH—$(CH_2CH_2NH)_g$—.

In certain instances, for example, when POLY represents a linear polymer segment, then preferably the total number of carbonyls present in the polymer alkanal is 0 or 2 or greater, where the total number of carbonyls does not include the aldehyde carbonyl(s). However, when the linker, X' includes one or more contiguous (—$CH_2CH_2O$—) segments, then preferably the total number of carbonyls present in the polymer alkanal is 0, or 1, or 2, or 3, or greater.

Referring back to structure I, in another preferred embodiment of the invention, when X' is oxygen or includes at least one (—$CH_2CH_2O$—) segment, and z' ranges from 2 to 12, then at least one of $R^1$ or $R^2$ in at least one occurrence is an organic radical as defined above or alternatively, the polymer is heterobifunctional. In such an instance where the polymer is heterobifunctional, the polymer segment, POLY, preferably possesses a reactive group at one terminus that is not hydroxy.

Preferably, the linker is hydrolytically stable, and may contain one or more of the following functional groups: amide, urethane, ether, thioether, or urea. However, hydrolytically degradable linkages, such as carboxylate ester, phosphate ester, orthoester, anhydride, imine, acetal, ketal, oligonucleotide, or peptide, may also be present in a linker of the invention. Heteroatom linkers such as O or S, are particularly preferred, as are linkers containing oligomeric —$(CH_2CH_2O)_b$— or —$(CH_2CH_2NH)_g$— segments as described above.

The Polymer Segment/Polymers for Preparing a Polymer Alkanal

As shown in the illustrative structures above, a polymer alkanal of the invention contains a water-soluble polymer segment. Representative POLYs include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine). POLY can be a homopolymer, an alternating copolymer, a random copolymer, a block copolymer, an alternating tripolymer, a random tripolymer, or a block tripolymer of any of the above. The water-soluble polymer segment is preferably, although not necessarily, a poly(ethylene glycol) or "PEG" or a derivative thereof.

The polymer segment can have any of a number of different geometries, for example, POLY can be linear, branched, or forked. Most typically, POLY is linear or is branched, for example, having 2 polymer arms. Although much of the discussion herein is focused upon PEG as an illustrative POLY, the discussion and structures presented herein can be readily extended to encompass any of the water-soluble polymer segments described above.

Any water-soluble polymer having at least one reactive terminus can be used to prepare a polymer alkanal in accordance with the invention and the invention is not limited in this regard. Although water-soluble polymers bearing only a single reactive terminus can be used, polymers bearing two, three, four, five, six, seven, eight, nine, ten, eleven, twelve or more reactive termini suitable for conversion to a polymer alkanal as set forth herein can be used. Advantageously, as the number of hydroxyl or other reactive moieties on the water-polymer segment increases, the number of available sites for introducing an alkanal group increases. Nonlimiting examples of the upper limit of the number of hydroxyl and/or reactive moieties associated with the water-soluble polymer segment include 500, 100, 80, 40, 20, and 10.

In turning now to the preferred POLY, PEG, "PEG" includes poly(ethylene glycol) in any of its linear, branched or multi-arm forms, including end-capped PEG, forked PEG, branched PEG, pendant PEG, and PEG containing one or more degradable linkage separating the monomer subunits, to be more fully described below.

To prepare a polymer alkanal of the invention, one commonly used PEG starting material is free PEG, a linear polymer terminated at each end with hydroxyl groups:

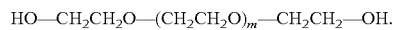

The above polymer, alpha-, omega-dihydroxylpoly(ethylene glycol), can be represented in brief form as HO-PEG-OH, and is also referred to herein as PEG-diol, where "-PEG-" in "HO-PEG-OH" corresponds to:

and (n) typically ranges from about 3 to about 4,000, or from about 3 to about 3,000, or more preferably from about 20 to about 1,000. In reference to structure I, POLY may for example, be a hydroxy-terminated PEG such as HO—CH$_2$CH$_2$O—(CH$_2$CH$_2$O)$_{n-1}$—CH$_2$CH$_2$—.

Another type of PEG useful for preparing the polymer alkanals of the invention is end-capped PEG, where PEG is terminally capped with an inert end-capping group. Preferred end-capped PEGs are those having as an end-capping moiety a group such as alkoxy, substituted alkoxy, alkenyloxy, substituted alkenyloxy, alkynyloxy, substituted alkynyloxy, aryloxy, substituted aryloxy. Preferred are end-capping groups such as methoxy, ethoxy, and benzyloxy.

Referring now to structures I and I-A through I-C, POLY, in certain embodiments, either is or comprises a poly(ethylene glycol) corresponding to the structure:

"Z—(CH$_2$CH$_2$O)$_n$—" or "Z—(CH$_2$CH$_2$O)$_n$—CH$_2$CH$_2$—", where n ranges from about 3 to about 4000, or from about 10 to about 4000, and Z is or includes a functional group such as hydroxy, amino, ester, carbonate, aldehyde, alkenyl, acrylate, methacrylate, acrylamide, sulfone, thiol, carboxylic acid, isocyanate, isothiocyanate, hydrazide, maleimide, vinylsulfone, dithiopyridine, vinylpyridine, iodoacetamide, alkoxy, benzyloxy, silane, lipid, phospholipid, biotin, and fluorescein. Again, the POLY structures shown immediately above may represent linear polymer segments, or may form part of a branched or forked polymer segment. In an instance where the polymer segment is branched, the POLY structures immediately above may, for example, correspond to the polymer arms forming part of the overall POLY structure. Alternatively, in an instance where POLY possesses a forked structure, the above POLY structure may, for example, correspond to the linear portion of the polymer segment prior to the branch point.

POLY may also correspond to a branched PEG molecule having 2 arms, 3 arms, 4 arms, 5 arms, 6 arms, 7 arms, 8 arms or more. Branched polymers used to prepare the polymer alkanals of the invention may possess anywhere from 2 to 300 or so reactive termini. Preferred are branched polymer segments having 2 or 3 polymer arms. An illustrative branched POLY, as described in U.S. Pat. No. 5,932,462, corresponds to the structure:

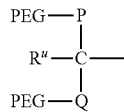

In this representation, R" is a nonreactive moiety, such as H, methyl or a PEG, and P and Q are nonreactive linkages. In a preferred embodiment, the branched PEG polymer segment is methoxy poly(ethylene glycol) disubstituted lysine.

In the above particular branched configuration, the branched polymer segment possesses a single reactive site extending from the "C" branch point for positioning of the reactive alkanal group via a linker. Branched PEGs such as these for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts.

One particular type of branched PEG alkanal corresponds to the structure: (MeO-PEG-)$_i$G-X'-alkanal, where i equals 2 or 3, and G is a lysine or other suitable amino acid residue.

An illustrative branched polymer alkanal of the invention has the structure shown below:

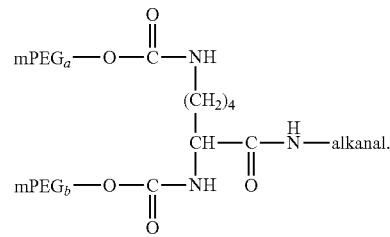

Structure V-A

In this instance, the linker corresponds to C(O)—NH, optionally containing an oligomeric —(CH$_2$CH$_2$O)$_b$— or —(CH$_2$CH$_2$NH)$_g$— segment positioned between the amide nitrogen and the alkanal portion of the polymer as shown in Structure V-B below. Exemplary oligomeric segments will possess b or g values ranging from about 1 to about 40, or from about 1 to about 30. Preferably b or g possess values of around 20 or less. Preferably, b or g will have one of the following values: 2, 3, 4, 5, 6, 7, 8, 9, 10, or greater. In a particularly preferred embodiment, b or g ranges from 2 to 6, and mPEG$_a$ and mPEG$_b$ are the same or are different.

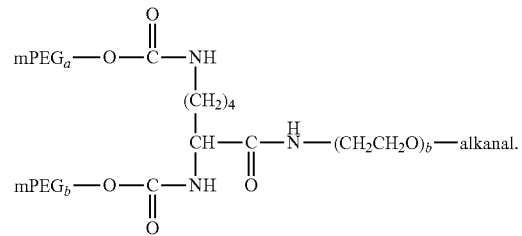

Structure V-B

Certain embodiments are preferred for polymer alkanals having a branched structure. For example, in one particular embodiment, for example when POLY in Structure I is branched, then at least one of R$^1$ or R$^2$ in at least one occurrence is an organic radical as defined above. In alternative preferred embodiment, for example, when POLY in Structure I is branched, then X' includes —(CH$_2$CH$_2$O)$_b$— where b is from 1 to about 20, in the instance where POLY comprises a lysine residue. On occasions when POLY has 2 polymer arms, it is preferable that neither polymer arm comprises oxygen as the only heteroatom in the instance where POLY comprises "C—H" as a branch point.

Branched PEGs for use in preparing a polymer alkanal of the invention additionally include those represented more generally by the formula G(PEG)$_n$, where G is a central or core molecule from which extends 2 or more PEG arms. The variable n represents the number of PEG arms, where each of the polymer arms can independently be end-capped or alternatively, possess a reactive functional group at its terminus, such as an alkanal or other reactive functional group. Branched PEGs such as those represented generally by the formula, G(PEG)$_n$, above possess 2 polymer arms to about 300 polymer arms (i.e., n ranges from 2 to about 300). Branched PEGs such as these preferably possess from 2 to about 25 polymer arms, more preferably from 2 to about 20 polymer arms, and even more preferably from 2 to about 15 polymer arms or fewer. Most preferred are multi-armed polymers having 3, 4, 5, 6, 7 or 8 arms.

Preferred core molecules in branched PEGs as described above are polyols. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

Multi-armed PEGs for use in preparing a polymer alkanal of the invention include multi-arm PEGs available from Nektar, Huntsville, Ala. In a preferred embodiment, a multi-armed polymer alkanal of the invention corresponds to the following, where the specifics of the alkanal portion of the molecule are provided elsewhere herein Further, the polymer segment may possess one or more weak or degradable linkages, such as ester linkages that are subject to hydrolysis. Other hydrolytically degradable linkages that may be contained in POLY include carbonate, imine, phosphate ester, and hydrazone.

Generally, the nominal average molecular mass of the water-soluble polymer segment, POLY will vary. The nominal average molecular mass of POLY typically falls in one or more of the following ranges: about 100 daltons to about 100,000 daltons; from about 500 daltons to about 80,000 daltons; from about 1,000 daltons to about 50,000 daltons; from about 2,000 daltons to about 25,000 daltons; from about 5,000 daltons to about 20,000 daltons. Exemplary nominal average molecular masses for the water-soluble polymer segment POLY include about 1,000 daltons, about 5,000 daltons, about 10,000 daltons, about 15,000 daltons, about 20,000 daltons, about 25,000 daltons, about 30,000 daltons, and about 40,000 daltons. Low molecular weight POLYs possess molecular masses of about 250, 500, 750, 1000, 2000, or 5000 daltons.

Structure XIII-A

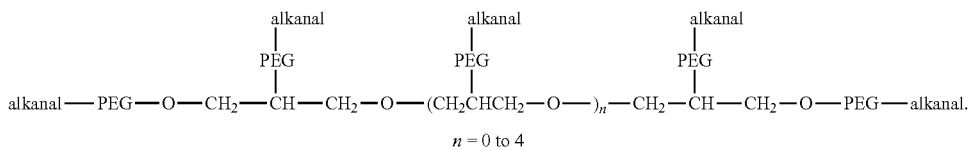

$n = 0$ to 4

Alternatively, the polymer alkanal may possess an overall forked structure. An example of a forked PEG corresponds to the structure: PEG-Y—CH—(X'—[C(R$^1$)(R$^2$)]$_{z'}$—CHO)$_2$, where PEG is any of the forms of PEG described herein, Y is a linking group, preferably a hydrolytically stable linkage, and the other variables corresponding to the linker and the alkanal portion are as defined above.

Additional illustrative forked PEG alkanals derivatives correspond to the following:

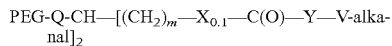

where PEG is any of the forms of PEG described herein. Q is a hydrolytically stable linkage, such as oxygen, sulfur, or —C(O)—NH—; m ranges from 1 to 10, (that is, m can equal 1, 2, 3, 4, 5, 6, 7, 8, 9, or 10) but is preferably m is 1, 2, 3, or 4; X is an optional atom, and when present, is O or N; Y is NH or O; and V is an optional oligomeric segment such as —(CH$_2$CH$_2$O)$_b$— or (CH2CH2NH)$_g$- as described previously. An exemplary branched PEG corresponding to "PEG" in the above formula is mPEG disubstituted lysine, where "PEG" corresponds to:

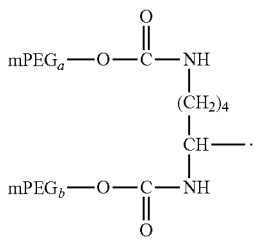

Alternatively, the PEG polymer segment for use in preparing a polymer alkanal of the invention may be a PEG molecule having pendant reactive groups along the length of the PEG chain rather than at the end(s), to yield a polymer alkanal having one or more pendant alkanal groups attached to the PEG chain by a linker, X'.

Representative Polymer Alkanals

Following the general description above, the following are some illustrative structures demonstrating preferred polymer alkanals in accordance with the invention.

For example, the polymer alkanal of the invention, when linear, may possess a homobifunctional or heterobifunctional structure according to structure II below. A homobifunctional structure according to the structure below is one where both termini are the same.

Structure II

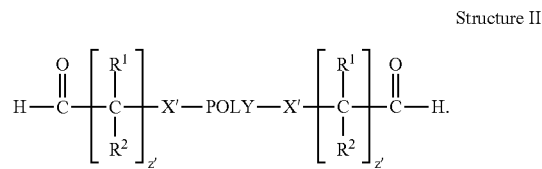

Preferred values for X' and —CR$^1$R$^2$— are as set forth above. Particularly preferred structures in accordance with structure II are those in which POLY is poly(ethylene glycol), and X' is —O—C(O)—NH—, —C(O)—NH—, —NH—C(O)—NH—, —O—C(O)—NH—(CH$_2$CH$_2$O)$_b$—, —C(O)—NH—(CH$_2$CH$_2$O)$_b$—, or —NH—C(O)—NH—(CH$_2$CH$_2$O)$_b$—, and z' ranges from 2 to about 12, and is more preferably 2, 3, 4, 5, or 6. More specifically, representative polymer alkanals of the invention include the following:

Structure III-A

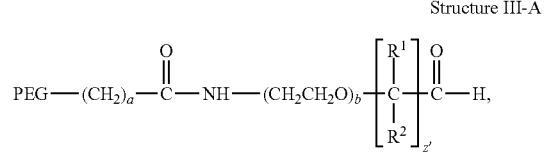

-continued

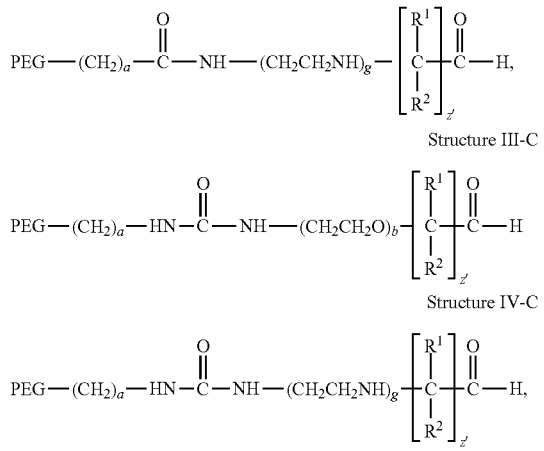

Structure IV-A

Structure III-C

Structure IV-C wherein PEG is poly(ethylene glycol), b and g are each independently 0 to 20, a is 0 to 6, and the remaining variables are as defined previously. Preferred are structures in which b and g range from 1 to 8 or alternatively range from 1 to about 6. Although z' ranges from 1 to about 21, preferred are structures in which z' ranges from 2 to 6, e.g., is 3 or 4.

Structural representations of two polymer alkanals where the variable "a" (as shown in the structures immediately above) is zero are provided below.

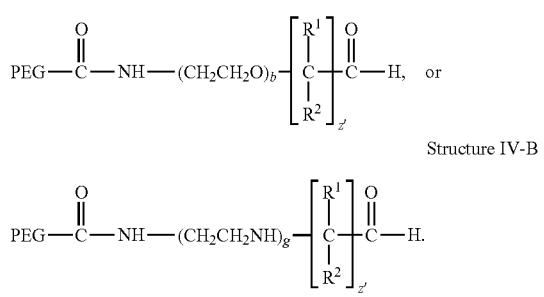

Structure III-B

Structure IV-B

An illustrative polymer butanal possesses the structure:

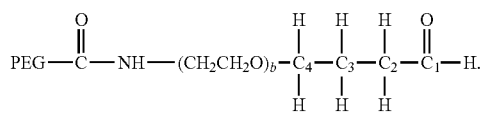

Structure III-D

Particularly preferred PEGs corresponding to Structure III-D above include $Z—(CH_2CH_2O)_n—$ or

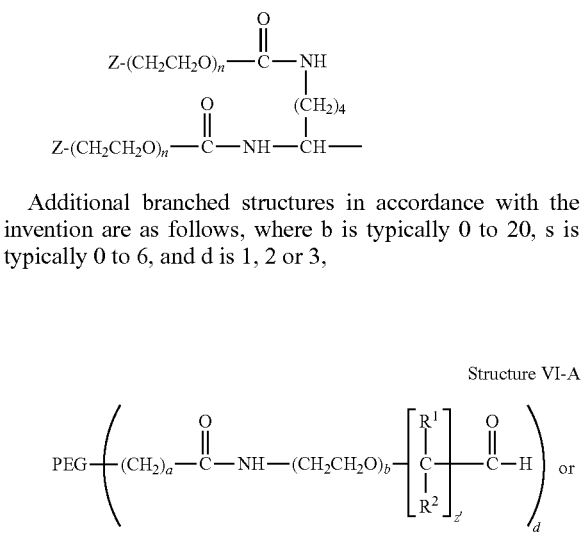

Additional branched structures in accordance with the invention are as follows, where b is typically 0 to 20, s is typically 0 to 6, and d is 1, 2 or 3, Structure VI-A Structure VI-B In Structures VI-A and B above, PEG can be linear or branched. Preferably, $R^1$ and $R^2$ in each occurrence are H, and z' ranges from 3 to 12, and is even more preferably 3, 4, 5, or 6. As one example, a polymer in accordance with Structure VI-B is one where PEG corresponds to the structure:

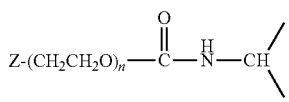

where Z is an end-capping or functional group as described previously.

Another illustrative polymer alkanal of the invention possesses the structure shown below:

Structure XIV

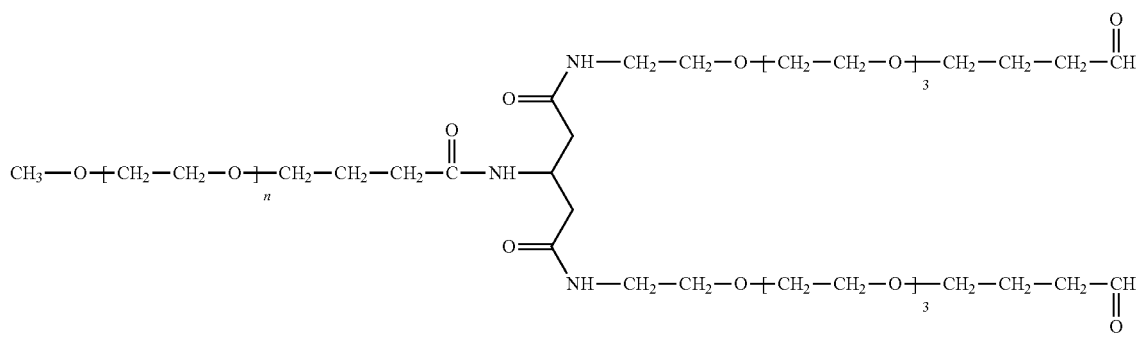

In the above embodiment, the polymer alkanal also has a forked structure and is suitable for covalent attachment to two biologically active agents. The above structure contains, in the portions extending from the —CH-branch point, a linker containing oligomeric —(CH$_2$CH$_2$O)— segments, where the number of such segments in each portion is 3. The number of such oligomeric segments in the above structure can be varied in accordance with the generalized description provided above.

Further exemplary polymer alkanal structures include the following, where the variables have been previously defined:

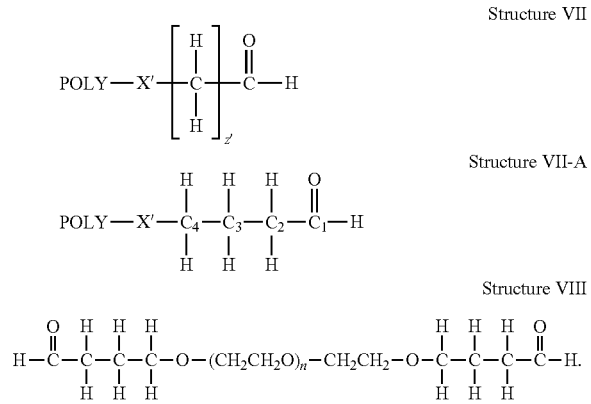

Structure VII

Structure VII-A

Structure VIII

Preferably, any one of the above structures is provided as a composition having one or more of the unique composition features described in greater detail below.

Features of the Polymer Alkanal Compositions Formed and Methods of Preparation

The polymer alkanals of the invention possess several advantages over previously prepared polymer aldehydes. First, the polymer alkanals are prepared in very high yields, in part due to the simplicity of the synthetic approach employed, particularly for the alkanals having oxygen as the linker moiety. Moreover, in examining the stability of the butanals of the invention, it was discovered that these types of alkanals are more stable at basic pHs than prior known polymer aldehyde derivatives (e.g., propionaldehydes, acetaldehydes), and are formed without significant or even detectable amounts of retro-Michael type reaction side products. For instance, as demonstrated in Example 3, under basic conditions, mPEG propionaldehyde undergoes a retro-Michael type reaction, producing mPEG-OH and the elimination product, acrolein, in significant quantities (after 24 hours at room temperature and pH 8, nearly 40% of the PEG-propionaldehyde had decomposed). In contrast, mPEG butyraldehyde is significantly more stable under basic conditions, demonstrating essentially no decomposition of this sort under the conditions employed.

Further, the butanal polymer derivative of the invention reaches equilibrium in water with its corresponding hydrate at about 50% hydrate, far lower than the 70% hydrate equilibrium exhibited by propionaldehyde and the 100% hydrate exhibited by acetaldehyde. The lower reactivity of the polymer derivatives of the invention is also evidenced by the markedly greater stability of the derivatives of the invention under basic conditions (see Example 3 below). No acrolein byproduct is observed during conjugation reactions between the aldehyde derivatives of the invention and proteins or other molecules at basic pH. The lower reactivity of the aldehyde derivatives of the invention suggests that the derivatives of the invention are more selective, meaning the inventive derivatives are capable of reacting with greater selectivity or specificity with specific amino groups, particularly N-terminal amino groups, on proteins or peptides, as opposed to nonselective or random reaction with any number of amino groups on a protein or peptide molecule. In many applications, selective N-terminal attachment of the polymer backbone is preferred to better preserve protein conformation and biological activity.

Moreover, the polymer alkanals of the invention are formed from the corresponding acetal precursors by hydrolysis under mild acidic conditions, i.e., under much less harsh acidic conditions than required for either PEG acetaldehyde or PEG propionaldehyde. If desired, such mild conditions allow direct in situ conjugation of the polymer derivatives of the invention with proteins, peptides, or other molecular targets without requiring an intervening isolation step. Further, due to the synthetic approaches employed, the polymer alkanals of the invention are also provided in high purity, often absent iodine-containing species or that can promote decomposition of the polymer segment.

Due to the mildness of the synthetic approach employed, and further due to the stable nature of the structures provided herein, the polymer alkanals of the invention are additionally provided as compositions that are essentially absent retro-Michael type reaction products. Thus, the polymer alkanal compositions provided herein are particularly storage stable, exhibiting very limited amounts if any of polymer decomposition. As an example, based on stability data collected over time, the polymer alkanals of the invention were found to exhibit less than about 10% degradation of the polymer aldehyde group when stored at 40° C. for 15 days. This percent degradation was determined by NMR analysis. Additionally, provided are linear mPEG polymer alkanals of the invention that are substantially free of the corresponding PEG-dialkanal (i.e., a homobifunctional PEG impurity arising from the presence of an amount of PEG-diol in the mPEG-OH raw material).

In turning now more specifically to the method for making a polymer alkanal of the invention, a polymer alkanal is generally prepared by reacting a water soluble polymer having at least one reactive group, Y, with a protected alkanal reagent containing a reactive group, K, suitable for displacement by or alternatively, reaction with Y, under conditions effective to form a water soluble polymer alkanal in protected form. Generally, a protected alkanal reagent will possess from about 2 to about 20 carbon atoms. The water soluble polymer alkanal in protected form thus formed is then typically hydrolyzed, for example, under acidic conditions to form the desired water soluble polymer alkanal.

Typically, the coupling reaction (i.e., the coupling of the reactive polymer and the protected alkanal reagent) is carried out in an organic solvent such as toluene, chloroform, methylene chloride, acetonitrile, acetone, dioxane, methanol, and ethanol. The reaction is preferably carried out under an inert atmosphere, at temperatures ranging from about 20° C. to about 150° C. Hydrolysis to form the desired alkanal is typically acid-promoted, and is conducted at pHs below 7.0, with preferred pHs ranging from about 3 to about 6.5. Hydrolysis can be carried out at a pH of about 3, 4, 5, or 6, with lower pHs around 3 being preferred.

Detailed examples of the synthetic approach outlined above are provided in Examples 1, 2, 5, and 17.

Most typically, the coupling of the polymer segment to the protected alkanal reagent proceeds via a Williamson ether synthesis. More specifically, the reactive group Y of the polymer is hydroxyl (which in the presence of a strong base is converted to its corresponding anionic or alkoxy form), and the reactive group K on the protected alkanal reagent acetal is a good leaving group, such as a halide (preferably Cl— or Br—) or methyl sulfate (a sulfonate ester), that can be readily displaced by the oxygen anion positioned at the polymer terminus. The resulting preferred linkage is an ether linkage (O—) connecting POLY to the alkanal.

Following attachment to POLY, the protected alkanal is hydrolyzed at an acidic pH to form the corresponding aldehyde or alkanal functional group. As noted above, the alkanal acetals such as butanal acetal are hydrolyzed under milder conditions than the corresponding propanal or ethanal acetals. For example, when z' is 3 or greater, an alkanal acetal of the invention can be hydrolyzed at a pH of about 3 or 4 or higher, particularly when $R^1$ and $R^2$ in all instances are H. As noted in Examples 2 and 4, the butanal acetal group described therein is hydrolyzed in about 3 hours at a pH of 3. The ability to form this alkanal functional group under mild acidic conditions is advantageous since it enables the in situ use of the aldehyde-functionalized polymer for conjugation to a protein or other biologically active molecule following neutralization of the solution containing the polymer alkanal to a suitable pH for conjugation (typically a pH of about 5 to about 10). In contrast, linear polymer propionaldehydes require isolation prior to conjugation due to the quantity of base required to neutralize the low pH solution and the correspondingly greater amount of salts generated during such a neutralization step.

In the method employed, the protected alkanal reagent is typically an acetal such as dimethyl acetal, diethyl acetal, di-isopropyl acetal, dibenzyl acetal, 2,2,2-trichloroethyl acetal, bis(2-nitrobenzyl)acetal, S,S'-dimethyl acetal, and S,S'-diethyl acetal. Alternatively, the acetal may be a cyclic acetal or a cyclic thioacetal.

More specifically, the protected alkanal will usually possess a structure as follows:

Structure XI-D.

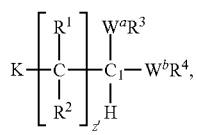

In this structure, z' is an integer from 1 to about 21. As for the polymer aldehydes provided above, $R^1$, in each occurrence, is independently H or an organic radical selected from the group consisting of alkyl, substituted alkyl, alkenyl, substituted alkenyl, alkynyl, substituted alkynyl, aryl, and substituted aryl; and $R^2$, in each occurrence, is independently H or an organic radical selected from the group consisting of alkyl, substituted alkyl, alkenyl, substituted alkenyl, alkynyl, substituted alkynyl, aryl, and substituted aryl. $W^a$ and $W^b$ are each independently O or S, and $R^3$ and $R^4$ are each independently H or an organic radical selected from the group consisting of methyl, ethyl, isopropyl, benzyl, 1,1,1-trichoroethyl, and nitrobenzyl, or when taken together, are —$(CH_2)_2$— or —$(CH_2)_3$—, forming a 5 or 6 membered ring when considered together with $W^a$, $C_1$, and $W^b$.

Preferably, K is one of the following reactive groups:

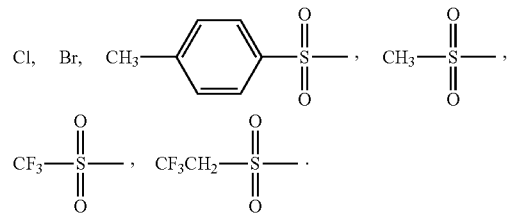

In this method, the polymer alkanal in protected form is typically formed in greater than about 85% yield, and even more preferably in greater than about 90 to 95% yield.

Following hydrolysis to obtain the desired aldehyde-functionalized polymer, the product may be isolated if desired by neutralizing the reaction mixture, e.g., raising the pH to from about 6.0 to about 7.5, followed by extraction of the polymer alkanal into an organic solvent, and removing the solvent, e.g., by rotary evaporation, lyophilization, or distillation.

Due to the simplicity of this approach that uses neither direct oxidative methods nor iodine-containing species to provide the desired aldehyde function, the products thus formed are highly pure, demonstrate enhanced storage stability in comparison to other known polymer aldehydes, and possess low polydispersity values (less than about 1.5, preferably less than about 1.2, and typically polydispersities less than about 1.1, 1.08, 1.05, 1.04, and 1.3). Polymers having polydispersities as low as 1.03, 1.02 and 1.01 have been thus prepared.

An isolated polymer alkanal of the invention will preferably have a purity of at least about 95%, based upon polymeric contaminants.

Examples 1 and 2 illustrate the formation of mPEG polymer alkanals. In instances in which the polymer starting material is PEG-diol, one of the PEG hydroxyl groups is generally protected prior to reaction with the protected alkanal reagent, followed by deprotection subsequent to coupling. All illustrative polymer protected alkanal thus formed is shown by Structure XI-E below.

Structure XI-E

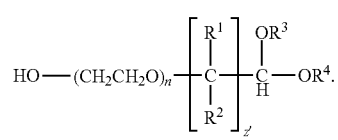

The hydroxy terminus of the PEG can then, if desired, be converted to a functional group to provide either a homobifunctional or a heterobifunctional protected alkanal. Suitable functional groups include amino, ester, carbonate, aldehyde, alkenyl, acrylate, methacrylate, acrylamide, sulfone, thiol, carboxylic acid, isocyanate, hydrazide, isothiocyanate, maleimide, vinylsulfone, dithiopyridine, vinylpyridine, iodoacetamide, and silane. Preferred are functional groups such as N-hydroxysuccinimidyl ester, benzotriazolyl carbonate, amine, vinylsulfone, and maleimide, N-succinimidyl carbonate, hydrazide, succinimidyl propionate, succinimidyl butanoate, succinimidyl succinate, succinimidyl ester, glycidyl ether, oxycarbonylimidazole, p-nitrophenyl carbonate, aldehyde, orthopyridyl-disulfide, and acrylol.

Other representative alkanal reagents are described by the structures:

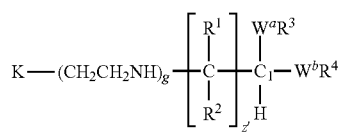

Structure XI-F

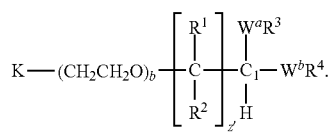

Structure XI-G

In yet another approach, a polymer alkanal of the invention is advantageously prepared from a chromatographically purified POLY-Y. In this way, polymer impurities, if present, and in particular difunctional impurities arising from PEG-diol, are removed to enable formation of an extremely pure polymer alkanal product as previously described. This approach is exemplified in Example 5. A summary of the overall synthetic approach employed, its advantages, its applicability to the general methods described herein, as well as specific details of the reactions carried out is provided in Example 5.

Although any chromatographic separation method may used, particularly preferred is ion-exchange chromatography, where the Y in POLY-Y is an ionizable group or is a derivative of an ionizable group such as a carboxylic acid, active ester, amine or the like.

Illustrative polymer alkanal acetals of the invention may possess any of the following structures, where the variables have been previously described:

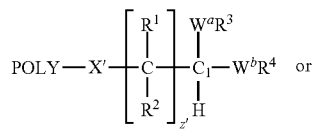

Structure IX

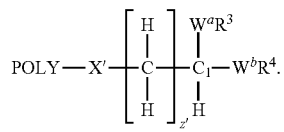

Structure IX-A

In yet another approach for preparing a polymer alkanal of the invention, a polymer alkanal can be prepared by building the polymer segment, POLY, directly onto an acetal precursor, e.g., by direct polymerization. More specifically, in this method, an acetal precursor having at least one active anionic site suitable for initiating polymerization is first provided. The anionic site of the acetal precursor is then contacted with a reactive monomer capable of polymerizing, to thereby initiate polymerization of the reactive monomer onto the acetal precursor. As a result of the contacting step, additional reactive monomers are added to the acetal precursor to form a polymer chain. The contacting is allowed to continue until a desired length of the polymer chain is reached, followed by terminating the reaction to achieve a polymer aldehyde precursor of the invention.

The resulting polymer aldehyde precursor can be further hydrolyzed to the corresponding alkanal as set forth above, if desired. Most preferably, the reactive monomer is ethylene oxide and the reactive anionic site contained within the acetal precursor is an alkoxide anion (O—), preferably accompanied by an alkali metal or other suitable counterion. The alkoxide end group present in the acetal precursor is active for anionic ring opening polymerization of ethylene oxide to form a polymer alkanal of the invention.

More particularly, the acetal precursor will generally possess a structure corresponding to:

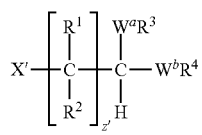

where the variables possess the values described above, with the exception that X' terminates in an oxygen anion, or O⁻ (e.g., in its neutral form, X' typically terminates in a hydroxyl group or —OH, that in the presence of a strong base, is converted to the corresponding alkoxide salt). Suitable counterions include Na⁺, K⁺, Li⁺, and Cs⁺. The terminating step generally comprises neutralizing the reaction, e.g., by addition of acid. Optionally, the polymer segment may be capped by addition of an alkylating reagent or other reagent suitable for providing a non-reactive terminus.

In one particular embodiment of the above method, POLY-Y corresponds to the structure Z—(CH₂CH₂O)ₙH, wherein n is from about 10 to about 4000, and Z is selected from the group consisting of —OCH₃, —OCH₂CH₃, and —OCH₂(C₆H₅). In a further embodiment, POLY-Y corresponds to the structure Z—(CH₂CH₂O)₆CH₂CH₂O⁻M⁺, where POLY-Y is prepared by anionic ring-opening polymerization of ethylene oxide onto an end-capped alcoholate salt such as Z—CH₂CH₂O⁻M⁺, prepared by metallation of the terminal —OH group of Z—CH₂CH₂OH with a strong base. M⁺ represents a metal counterion such as Na⁺, K⁺, Li⁺, Cs⁺, Rb⁺. POLY-Y thus prepared is then suitable for reaction with a protected alkanal reagent as described above.

A generalized scheme outlining this approach is provided herein as FIG. 1, and the conditions for carrying out such a reaction or series of reactions are provided in Example 15.

Storage of Polymer Alkanal Reagents

Preferably, the polymer alkanals of the invention are stored under an inert atmosphere, such as under argon or under nitrogen, since the aldehyde functionality can react with atmospheric oxygen to produce the corresponding carboxylic acid. Due to the potential for reaction of the aldehyde portion of the molecule with water (e.g., by exposure to moisture to form the corresponding hydrate), it is also preferable to minimize exposure of the polymer alkanals of the invention to moisture. Thus, preferred storage conditions are under dry argon or another dry inert gas at temperatures below about −15° C. Storage under low temperature conditions reduces the rate of hydrolysis of the polymer aldehyde to the corresponding hydrate form. Additionally, in instances where the polymer segment of the polymer alkanal is PEG, the PEG portion of the alkanal can react slowly with oxygen to form peroxides along the PEG portion of the molecule. Formation of peroxides can ultimately lead to chain cleavage, thus increasing the polydispersity of the PEG alkanal reagent. In view of the above, it is additionally preferred to store the PEG alkanals of the invention in the dark.

Biologically Active Conjugates
Coupling Chemistry
Conjugation to Proteins—Random and N-Terminal Selective The above-described polymer alkanals are useful for conjugation to biologically active agents or surfaces bearing at least one amino group available for reaction. Typically, a PEG aldehyde of the invention is coupled to an amino group by reductive amination, resulting in formation of a secondary amine linkage between the polymer segment and the surface or biologically active agent. In conjugating a polymer alkanal of the invention with an amino-bearing biologically active agent or surface, the polymer alkanal is reacted with the target amino-bearing molecule in a suitable solvent to form the corresponding imine-linked intermediate, which is then reduced to form a secondary amine linkage between the polymer and the biologically active agent or surface. Reduction of the imine to the corresponding amine is accomplished by addition of a reducing agent. Exemplary reducing agents include sodium cyanoborohydride, sodium borohydride, lithium aluminum hydride, and the like.

Generally, the polymer aldehydes of the invention can be used to selectively target the modification of the N-terminus under conditions that differentiate the reactivity of the alpha amine at the N-terminal amino acid. Certain polymer alkanals of the invention appear to demonstrate a greater selectivity than previously known aldehyde derivatives and, thus, are more suitable for applications where selective N-terminus protein modification is desired. Reaction conditions for preparing an N-terminally modified protein or peptide include (i) dissolving the protein or peptide to be modified in a non-amine-containing buffer (e.g., at a pH range from about 4 to about 6.5, preferably from about 5 to 6.5, most preferably at a pH of about 5 to 5.5), (ii) adding to the protein or peptide solution a polymer alkanal of the invention, (iii) allowing the protein or peptide and polymer alkanal to react to form the imine-coupled polymer conjugate, followed by (iv) addition of a reducing agent to form the corresponding secondary amine coupled polymer conjugate. Reaction conditions for random attachment of a polymer alkanal are essentially identical to those described above, with the exception that the pH is somewhat higher (to be discussed in greater detail below).

To favor N-terminus modification, a pH of about 5 to 5.5 is most preferred since it is believed to facilitate selective N-terminus modification due to differences in the pKa value of the amino group of an N-terminal amino acid and the amino group of lysines. Generally speaking, conditions favoring N-terminal selectivity include pHs below 7, and typically not lower than about 4. The most favorable pH for promoting N-terminal selectivity can be determined by one skilled in the art, and will depend upon the particular protein to be modified. Suitable buffers for conducting conjugation include sodium phosphate, sodium acetate, sodium carbonate, and phosphate buffered saline (PBS). Typically, the polymer alkanal is added to the protein-containing solution at an equimolar amount or at a molar excess relative to target protein. The polymer alkanal is added to the target protein at a molar ratio of about 1:1 (polymer alkanal:protein), 1.5:1, 2:1, 3:1, 4:1, 5:1, 6:1, 8:1, or 10:1. Molar excesses of PEG-alkanal relative to target protein are typically in the range of about 2 to 5. The reductive amination reaction is typically carried out at temperatures at or below about room temperature (25° C.), although temperatures may range from about −15° C. to about 100° C., more preferably from about 4° C. to 37° C., for approximately one to twenty four hours. The reducing agent is also typically added in excess, that is to say, in amounts ranging from about a 2-fold to a 30-fold molar excess relative to polymer-protein conjugate. Preferred is to add the reducing agent in a 10-fold to 20-fold molar excess relative to polymer-protein conjugate. The exact reaction time is determined by monitoring the progress of the reaction over time. Progress of the reaction is typically monitored by withdrawing aliquots from the reaction mixture at various time points and analyzing the reaction mixture by SDS-PAGE or MALDI-TOF mass spectrometry or any other suitable analytical method. The resulting pegylated conjugates are further characterized using analytical methods such as MALDI, capillary electrophoresis, gel electrophoresis, and/or chromatography.

More specifically, to couple an aldehyde polymer derivative to a protein or peptide, a number of different approaches may be employed. One approach (i.e., a random pegylation approach) is to covalently attach PEG to any number of lysine residues that are surface accessible. To conduct such a reaction, a protein or peptide (such as those exemplary biomolecules provided below) is typically reacted with a polymer alkanal of the invention in a non amine-containing buffer at mild pHs generally ranging from about 5 to 8. (Non-amine containing buffers are preferred since the amino-groups in the buffer can compete with protein amino groups for coupling to the polymer alkanal). A suitable non-amine containing buffer is selected having an appropriate pK for the desired pH range for conducting the conjugation chemistry. The coupling reaction generally takes anywhere from minutes to several hours (e.g., from 5 minutes to 24 hours or more), and on average, coupling is achieved between about 0.2 and 4 hours to form the imine-coupled conjugate. To the reaction mixture is then added any one of a number of suitable reducing agents as described above (e.g., sodium cyanoborohydride). The resulting mixture is then generally allowed to react under low to ambient temperature conditions, e.g., 4° C. to 37° C. for about one hour to 48 hrs. Preferably, the reduction reaction is complete in less than about 24 hours. Random coupling is favored at pHs around 7 to 7.5 or so, while coupling at the N-terminal is favored at low pHs (e.g., around 5.5 or so).

To increase the degree of modification, that is, to promote an increase in the number of PEGs that are covalently attached at available sites on the target molecule, any one or more of the above described conditions (e.g., molar ratio of polymer alkanal to protein or peptide, temperature, reaction time, pH, etc.) can be increased, either independently or simultaneously. Regardless of the molecular weight of the PEG alkanal employed, the resulting product mixture is preferably but not necessarily purified to separate out excess reagents, unpegylated protein (or any target molecule), multi-pegylated conjugates, and free or unreacted PEG alkanal.

The random pegylation of illustrative proteins is provided in Examples 4 and 6. Site selective pegylation of illustrative proteins is described in Examples 7 to 13.

Characterization/Optional Separation of PEG-mers

Optionally, conjugates produced by reacting a PEG aldehyde of the invention with a biologically active agent are purified to obtain/isolate different PEGylated species. Alternatively, and more preferably for lower molecular weight PEGs, e.g., having molecular weights less than about 20 kilodaltons, preferably less than or equal to about 10 kilodaltons, the product mixture can be purified to obtain a distribution around a certain number of PEGs per protein molecule. For example, the product mixture can be purified to obtain an average of anywhere from one to five PEGs per protein, typically an average of about 3 PEGs per protein. The strategy for purification of the final conjugate reaction mixture will depend upon a number of factors—the molecular weight of the polymer employed, the particular protein, the desired dosing regimen, and the residual activity and in vivo properties of the individual conjugate(s) species.

If desired, PEG conjugates having different molecular weights can be isolated using gel filtration chromatography. That is to say, gel filtration chromatography is used to fractionate different PEG-mers (1-mer, 2-mer, 3-mer, etc.) on the basis of their differing molecular weights (where the difference corresponds essentially to the average molecular weight of the PEG chains). For example, in an exemplary reaction where a 100 kDa protein is randomly conjugated to a PEG alkanal having a molecular weight of about 20 kDa, the resulting reaction mixture will likely contain unmodified protein (MW 100 kDa), mono-pegylated protein (MW 120 kDa), di-pegylated protein (MW 140 kDa), etc. While this approach can be used to separate PEG conjugates having different molecular weights, this approach is generally ineffective for separating positional isomers having different pegylation sites within the protein. For example, gel filtration chromatography can be used to separate from each other mixtures of PEG 1-mers, 2-mers, 3-mers, etc., although each of the recovered PEG-mer compositions may contain PEGs attached to different reactive amino groups (e.g., lysine residues) within the protein.

Gel filtration columns suitable for carrying out this type of separation include Superdex™ and Sephadex™ columns available from Amersham Biosciences. Selection of a particular column will depend upon the desired fractionation range desired. Elution is generally carried out using a non-amine based buffer, such as phosphate, acetate, or the like. The collected fractions may be analysed by a number of different methods, for example, (i) OD at 280 nm for protein content, (ii) BSA protein analysis, (iii) iodine testing for PEG content (Sims G. E. C., et al., *Anal. Biochem,* 107, 60-63, 1980), or alternatively, (iv) by running an SDS PAGE gel, followed by staining with barium iodide.

Separation of positional isomers is carried out by reverse phase chromatography using an RP-HPLC C18 column (Amersham Biosciences or Vydac) or by ion exchange chromatography using an ion exchange column, e.g., a Sepharose™ ion exchange column available from Amersham Biosciences. Either approach can be used to separate PEG-biomolecule isomers having the same molecular weight (positional isomers).

Storage

Depending upon the intended use for the resulting PEG-conjugates, following conjugation, and optionally additional separation steps, the conjugate mixture may be concentrated, sterile filtered, and stored at low temperatures from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized protein conjugate powder formulation is absent residual buffer. Alternatively, a buffer exchange step may be used using a formulation buffer, so that the lyophilized conjugate is in a form suitable for reconstitution into a formulation buffer and ultimately for administration to a mammal.

Small Molecule Conjugation

The conjugation of a PEG-alkanal of the invention to a small molecule such as amphotericin B is conducted generally as described in Example 14, although precise reaction conditions will vary according to the small molecule being modified. Typically, the conjugation is conducted using a slight molar excess of PEG reagent relative to small molecule, e.g., about 1.2-1.5, to about a 5 to 10-fold molar excess. In some instances, depending upon the molecule, the small molecule drug may actually be used in excess, such as when the PEG-small molecule conjugate precipitates in the reaction solvent, e.g., ether, while the unreacted drug remains in solution.

Target Molecules and Surfaces

The reactive polymer alkanals of the invention may be attached, either covalently or non-covalently, to a number of entities including films, chemical separation and purification surfaces, solid supports, metal/metal oxide surfaces such as gold, titanium, tantalum, niobium, aluminum, steel, and their oxides, silicon oxide, macromolecules, and small molecules. Additionally, the polymers of the invention may also be used in biochemical sensors, bioelectronic switches, and gates. The polymer alkanals of the invention may also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymer of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, antiepileptics, bronchodilators, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer alkanal of the invention possesses a native amino group, or alternatively, is modified to contain at least one reactive amino group suitable for coupling to a polymer alkanal of the invention.

Specific examples of active agents suitable for covalent attachment to a polymer of the invention include but are not limited to asparaginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922, 675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer of the invention include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicillinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer alkanal of the invention are those having at least one amino group. Preferred molecules include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer alkanal of the invention include EPO, IFN-α, IFN-β, IFN-γ, consensus IFN, Factor VII, Factor VIII, Factor IX, IL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitis-B vaccine, rDNAse, alpha-1 proteinase inhibitor, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted, deleted, or the like, as long as the resulting variant protein possesses at least a certain degree of activity of the parent (native) protein.

Pharmaceutical Compositions

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

All articles, books, patents, patent publications and other publications referenced herein are incorporated by reference in their entireties.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Materials and Methods.

All PEG reagents referred to in the appended examples are commercially available unless otherwise indicated. All NMR data was generated by a 300 MHz NMR spectrometer manufactured by Bruker.

Lysozyme was obtained from Sigma.

Example 1

Synthesis of mPEG (2K)-Butyraldehyde

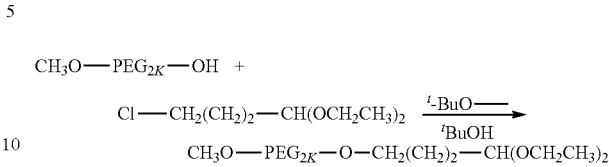

A. Preparation of mPEG (2K Da)-Butyraldehyde, diethyl acetal

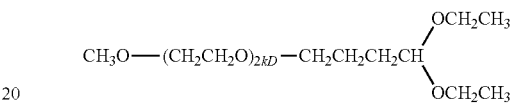

A mixture of mPEG (2K Da) (2.0 g) and toluene (30 mL) was azeotropically dried by distilling off toluene under reduced pressure. The dried mPEG, molecular weight, 2 kilodaltons, was dissolved in anhydrous toluene (15 ml) to which was added a 1.0 M solution of potassium tert-butoxide in tert-butanol (4.0 ml, 0.004 moles) and 4-chlorobutyraldehyde diethyl acetal (0.5 g, 0.00277 moles) (Alfa Aesar). The mixture was stirred at 100-105° C. overnight under an argon atmosphere. After cooling to room temperature, the mixture was filtered and added to 150 ml ethyl ether at 0-5° C. The precipitated product was filtered off and dried under reduced pressure. Yield: 1.6 g. The reaction proceeded in essentially a quantitative yield. That is to say, essentially all of the mPEG starting material was converted to the corresponding diethyl acetal, based upon the absence of hydroxyl protons corresponding to mPEG-OH starting material according to $^1$H NMR.

NMR (d$_6$-DMSO): 1.09 ppm (t, CH$_3$—C—) 1.52 ppm (m, C—CH$_2$—CH$_2$—), 3.24 ppm (s, —OCH$_3$), 3.51 ppm (s, PEG backbone), 4.46 ppm (t, —CH, acetal).

B. Preparation of mPEG (2 kD)-Butyraldehyde

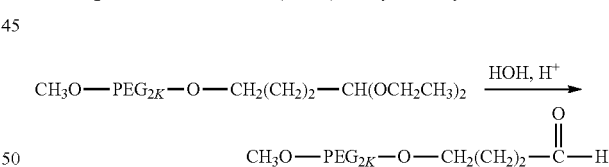

A mixture of mPEG (2K Da) butyraldehyde, diethyl acetal (1.0 g) from A. above, deionized water (20 ml), and an amount of 5% phosphoric acid to adjust the pH to 3.0, was stirred for 3 hours at room temperature. To this mixture was added sodium chloride (1.0 g) and the pH was adjusted to 6.8 by addition of 0.1 M sodium hydroxide. The product, mPEG (2 kD) butyraldehyde, was extracted with dichloromethane (3×20 ml). The extract was dried with anhydrous magnesium sulfate and the solvent was distilled off under reduced pressure to provide the mPEG butyraldehyde product in isolated form. Yield: 0.72 g.

The reaction proceeded in essentially a quantitative yield. That is to say, essentially all of the mPEG butyraldehyde diethyl acetal was converted to the corresponding aldehyde, based upon the absence of hydroxyl protons corresponding to mPEG-OH starting material as well as absence of hydroxyl protons corresponding to diethyl acetal according to $^1$H NMR.

NMR (d$_6$-DMSO): 1.75 ppm (p, —CH$_2$—CH$_2$—CHO—) 2.44 ppm (dt, —CH$_2$—CHO), 3.24 ppm (s, —OCH$_3$), 3.51 ppm (s, PEG backbone), 9.66 ppm (t, —CHO).

Example 2

Synthesis of mPEG (30 kD)-Butyraldehyde

A. Preparation of mPEG (30K Da)-Butyraldehyde, diethyl acetal, mPEG$_{30K}$—O—CH$_2$(CH$_2$)$_2$—CH(OCH$_2$CH$_3$)$_2$ A mixture of mPEG (30 kD) (60% solution in toluene, 3.30 g), toluene (30 ml) and BHT (butylated hydroxytoluene, 0.004 g) was azeotropically dried by distilling off the solvent under reduced pressure. The dried mPEG 30K was dissolved in anhydrous toluene (15 ml), and to this solution was added 1.0 M potassium tert-butoxide in tert-butanol (4.0 ml, 0.004 moles), 4-chlorobutyraldehyde diethyl acetal (0.5 g, 0.00277 moles) (Alfa Aesar), and potassium bromide (0.05 g). The resulting mixture was stirred overnight at 105° C. under argon atmosphere. The mixture was filtered, concentrated to dryness under reduced pressure and the crude product was dissolved in 20 ml of dichloromethane. This product-containing solution was added to ethyl ether (300 ml) at room temperature to precipitate the product. The precipitated product was isolated by filtration and dried under reduced pressure. Yield: 1.92 g.

NMR (d$_6$-DMSO): 1.09 ppm (t, CH$_3$—C—) 1.52 ppm (m, C—CH$_2$—CH$_2$—), 3.24 ppm (s, —OCH$_3$), 3.51 ppm (s, PEG backbone), 4.46 (t, —CH, acetal).

Based upon yields and analysis of the product, substitution of the acetal reagent at the hydroxy-terminus of the mPEG-OH reagent proceeded at a very high efficiency, that is to say, at essentially 100% substitution. The resulting product, without requiring further purification, was produced in high purity, without detectable or significant amounts of unreacted mPEG-OH. Typically, the alkanal or acetal polymers of the invention are produced in high purities—that is to say, typically, the desired alkanal product is present in the final composition in at least 85% purity, preferably at least 90% purity, and even more preferably, in at least 95% purity.

B. Preparation of mPEG (30K Da)-Butyraldehyde, mPEG$_{30K}$—O—CH$_2$(CH$_2$)$_2$—C(O)H A mixture of mPEG (30K Da) butyraldehyde, diethyl acetal (1.0 g), from A. above, deionized water (20 mL), and an amount of 5% phosphoric acid to adjust the pH to 3.0 was stirred for 3 hours at room temperature. To this mixture was added sodium chloride (1.0 g), and the pH was adjusted to 6.8 by addition of 0.1 M sodium hydroxide. The product was extracted with dichloromethane (3×20 ml). The extract was dried with anhydrous magnesium sulfate and the solvent was removed by distillation. The wet product was dried under reduced pressure. Yield: 0.82 g.

NMR (d$_6$-DMSO): 1.75 ppm (p, —CH$_2$—CH$_2$—CHO—) 2.44 ppm (dt, —CH$_2$—CHO), 3.24 ppm (s, —OCH$_3$), 3.51 ppm (s, PEG backbone), 9.66 ppm (t, —CHO).

Substitution: ~100%.

Conversion to the corresponding aldehyde proceeded in essentially quantitative yield.

Example 3

Comparative Stability of mPEG-Propionaldehyde and mPEG-Butyraldehyde at Basic pH Methoxy-PEG-propionaldehyde and mPEG-butyraldehyde were each exposed to high pH conditions for prolonged periods of time to compare the relative stability of each polymer under basic pH conditions. As indicated below, significant amounts of propionaldehyde PEG reacted under these conditions to form mPEG-OH and release acrolein (due to a retro-Michael type reaction), while no loss of the PEG butyraldehyde compound was detected. The details of this experiment are provided below.

A. Stability of mPEG(2K Da)-Butyraldehyde at Basic pH mPEG(2K Da)-butyraldehyde (from Example 1) (0.5 g) was dissolved in 10 ml 5 mM phosphate buffer (pH=8.0) and the resulting solution was stirred for 24 h at room temperature. NaCl (0.5 g) was added and the product was extracted with methylene chloride (3×10 ml). The extract was dried with anhydrous magnesium sulfate and the solvent was distilled off under reduced pressure at 25° C.

Based upon $^1$H NMR analysis, the product was unchanged. That is to say, no decomposition of the PEG-butanal was detected, even after an extended period of time under these basic pH conditions.

B. Stability of mPEG(5K Da)-Propionaldehyde at Basic pH mPEG(5K Da)-Propionaldehyde (Shearwater Corporation, aldehyde substitution 82%) (0.5 g), was dissolved in 10 ml 5 mM phosphate buffer (pH=8.0). The resulting solution was stirred for 24 h at room temperature. Gas chromatography headspace analysis showed that the solution contained acrolein (CH$_2$=CH—CHO); resulting from an elimination reaction under basic conditions such as those typically employed for protein conjugation. NaCl (0.5 g) was added and the product was extracted with methylene chloride (3×10 ml). The extract was dried with anhydrous magnesium sulfate and the solvent was distilled off under reduced pressure at 25° C.

Based upon $^1$H NMR analysis, the substitution of mPEG (5K Da)-propionaldehyde dropped to 62% (that is to say, 38% of the PEG-propanal had decomposed), and the product contained a substantial amount of mPEG-OH, arising from the loss of the C-3 segment corresponding to the propanal portion of the PEG-propanal.

Example 4

PEGylation of Lysozyme

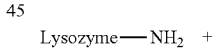

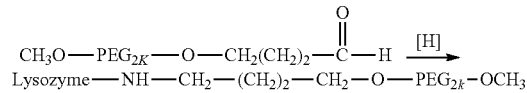

("Lysozyme-NH$_2$" is meant to indicate the lysozyme molecule with one of its reactive amino groups shown).

A. Random Pegylation Using a 2 kD PEG alkanal. The model protein, lysozyme, an 129 amino acid secretory enzyme, was used to demonstrate coupling of an alkanal polymer of the invention to an illustrative protein. Lysozyme contains six lysine residues as potential sites for pegylation.

Lysozyme (2.1 mg) was dissolved in 1 ml of 50 mM phosphate buffer (pH 7.6) to which was added mPEG (2 kD)-butyraldehyde (from Example 1, 1.5 mg). To this solution was added the reducing agent, NaCNBH$_3$ (sodium cyanoborohydride), and the solution was stirred for 24 h at room temperature. The resulting lysozyme conjugate possesses PEG chains coupled to lysozyme amino groups by an intervening —(CH$_2$)$_4$-chain.

The reaction product was analyzed by Matrix Assisted Laser Desorption Ionization Time-of-Flight (MALDI-TOF) mass spectrometry and displayed peaks corresponding to three PEGylated species of lysozyme at 16208 Da, 18422 Da, and 20520 Da, differing in mass by approximately 2000 Da (corresponding to the size of the PEG butanal reagent), as well as unmodified protein. The mass of unmodified (native) lysozyme by MALDI-TOF was determined to be 14153. Thus, the conjugate formed was really a mixture of monopegylated protein, di-pegylated protein, and tri-pegylated protein (1-mer, 2-mer and 3-mer).

The above demonstrates random pegylation of an illustrative protein of the invention to yield a distribution of pegylated products. If desired, the reaction mixture can be further separated to isolate the individual PEG conjugates, that is, lysozyme having one PEG molecule attached thereto, lysozyme having two PEGs attached, and lysozyme having three PEGs attached. Within each of the conjugate compositions described above (1-mer, 2-mer, 3-mer), the PEG molecule may be attached to different reactive amino sites within the lysozyme molecule.

B. PEGylation Using A 5 kD PEG Alkanal, mPEG-2-Methylbutyraldehyde

Conjugation of the model protein, lysozyme, is repeated using the alpha branched PEG reagent, mPEG$_{5kD}$-2-methylbutyraldehyde. Lysozyme (3 mg) is dissolved in approximately 1 mL of sodium phosphate buffer at a pH ranging from about 5.5 to 7.5. A two to five-fold molar excess of the PEG reagent, mPEG$_{5kD}$-2-methylbutyraldehyde, is added to the lysozyme solution, and the resulting solution is placed on a rotary mixer and allowed to react at room temperature. After approximately 15 minutes, a 20-fold molar excess of NaCNBH$_3$ is added and the reaction allowed to continue. Aliquots are withdrawn at various time intervals (4 hours, 8 hours, 12 hours, 16 hours, etc.) and the reaction progress is monitored by SDS-PAGE and MALDI-TOF mass spectrometry.

Upon completion of the reaction, the resulting conjugate mixture is concentrated, sterile filtered, and stored under low temperature conditions (−20° C. to −80° C.) until further use.

Example 5

Preparation of Branched PEG2(40.3 KDa)-Butyraldehyde

The preparation of an exemplary polymer alkanal having a branched PEG segment is provided below.

SUMMARY. The overall synthesis involved first the coupling of a tetra(ethylene glycol) spacer to a reactive alkanal precursor, 4-chlorobutyraldehyde diethyl acetal. The introduction of an oligomeric ethylene glycol spacer provides greater stability to the resulting product by extending the chain length between the reactive aldehyde (or acetal) group and a reactive group that may be contained in the linker moiety, X', thereby minimizing the occurrence of potential side reactions and improving yields.

The use of an oligomeric spacer, such as tetraethylene glycol, also provides a reactive functional group, in this instance, hydroxy, that can be converted, if necessary, for coupling to a polymer segment that has been chromatographically purified to remove polymeric impurities such as PEG-diol, mPEG-OH, and the like. In this way, undesired functionalized polymeric impurities such as PEG-dialdehyde (resulting from PEG diol) and the like are removed from the PEG segment prior to coupling to the alkanal precursor to provide the ultimate product, a water soluble polymer alkanal that is essentially free of polymeric impurities.

Turning to the specific reaction below, the coupling of the tetra(ethylene glycol) spacer to 4-chlorobutyraldehyde diethyl acetal leads to formation of the desired mono-alkanal product contaminated with di-alkanal product and starting tetra(ethylene glycol). However, a straightforward work-up that utilizes the differences in solubility of all of the components in the reaction mixture allows for the ready preparation of highly pure monoalkanal product, that is to say, having the alkanal (acetal) function substituted on only one of the reactive hydroxy groups of the tetra(ethylene glycol) molecule. (REACTION A.). The product from REACTION A was then converted to the corresponding mesylate by reaction with methanesulfonyl chloride, i.e., the free hydroxy group of the tetra (ethylene glycol) was converted first to the mesylate (REACTION B), followed by conversion of the mesylate to a primary amino group (REACTION C). The reactive amino group of the acetal reagent was then coupled to an illustrative branched polymer backbone segment having a reactive carbonyl carbon suitable for reaction with the amino group of the acetal reagent. The precursor to the PEG reactant, mPEG-disubstituted lysine, was purified by ion exchange chromatography prior to conversion to the corresponding activated ester to remove polymeric impurities. The N-hydroxysuccinimidyl ester of mPEG-disubstituted lysine was then reacted with an amino-alkanal acetal, via formation of an amide bond, to form the resulting branched PEG-spacer-alkanal acetal. The acetal was then readily hydrolyzed in the acid-catalyzed reaction to form the corresponding alkanal, and in particular, the 2-arm branched PEG (40 KDa) butyraldehyde.

This synthetic approach, i.e., is not limited to branched polymer segments but may be employed for polymer segments having any of the herein described geometries.

Summary of Overall Synthesis:

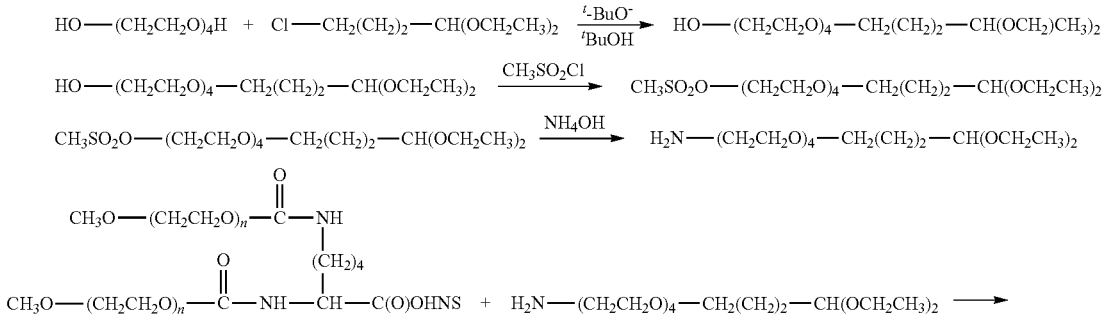

-continued

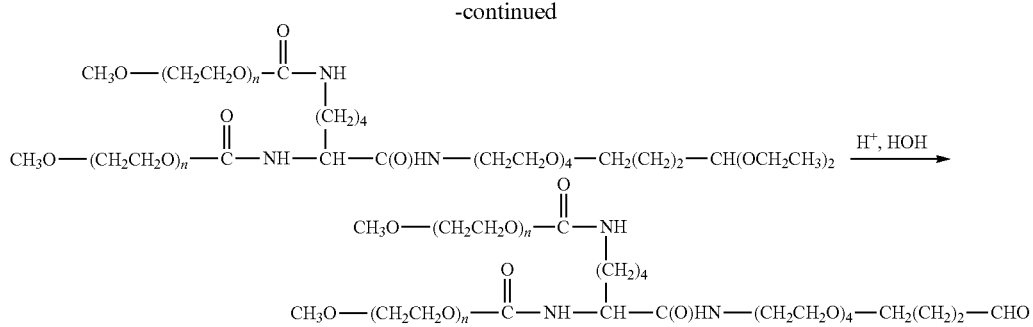

A. Tetra(ethylene glycol) mono-butyraldehyde, diethyl acetal, HO—(CH$_2$CH$_2$O)$_4$—CH$_2$CH$_2$O—CH$_2$(CH$_2$)$_2$—CH(OCH$_2$CH$_2$)$_2$ A mixture of tetra(ethylene glycol) (97.1 g, 0.500 moles) and toluene (200 ml) was azeotropically dried by distilling off toluene under reduced pressure (rotary evaporator). The dried tetra(ethylene glycol) was dissolved in anhydrous toluene (180 ml) and 1.0 M solution of potassium tert-butoxide in tert-butanol (120.0 ml, 0.120 moles) and 4-chlorobutyraldehyde diethyl acetal (18.1 g, 0.100 moles) (Alfa Aesar) were added. The mixture was stirred at 95-100° C. overnight under argon atmosphere. After cooling to room temperature, the mixture was filtered and the solvents were distilled off under reduced pressure. The crude product was dissolved in 1000 ml deionized water and the resulting solution was filtered through active carbon. Sodium chloride (10 g) was added and the product was extracted with dichloromethane (250, 200, and 150 ml). The extract was dried (over MgSO$_4$) and the solvent was distilled off under reduced pressure (by rotary evaporation).

The crude product was dissolved in 300 ml 10% phosphate buffer (pH=7.5) and impurities were extracted with ethyl acetate (2×50 ml). The product was extracted with dichloromethane (200, 150, and 100 ml). The extract was dried (over MgSO$_4$) and the solvent was distilled off under reduced pressure (by rotary evaporation).

Yield: 20.3 g. NMR (d$_6$-DMSO): 1.10 ppm (t, CH$_3$—C—) 1.51 ppm (m, C—CH$_2$—CH$_2$—), 3.49 ppm (bm, —OCH$_2$CH$_2$O—), 4.46 ppm (t, —CH, acetal), 4.58 ppm (t, —OH).

Purity: ~100% (no signs of unreacted starting materials).

B. Tetra(ethylene glycol)-α-mesylate-ω-butyraldehyde, diethyl acetal, CH$_3$—S(O)$_2$—O—(CH$_2$CH$_2$O)$_4$—CH$_2$CH$_2$O—CH$_2$(CH$_2$)$_2$—CH(OCH$_2$CH$_2$)$_2$ A mixture of tetra(ethylene glycol) mono-butyraldehyde, diethyl acetal (12.5 g, 0.037 moles) and toluene (120 ml) was azeotropically dried by distilling off toluene under reduced pressure (rotary evaporator). The dried tetra(ethylene glycol) mono-butyraldehyde, diethyl acetal was dissolved in anhydrous toluene (100 ml). To the solution was added 20 ml of anhydrous dichloromethane and 5.7 ml of triethylamine (0.041 moles). Then 4.5 g of methanesulfonyl chloride (0.039 moles) was added dropwise. The solution was stirred at room temperature under a nitrogen atmosphere overnight. Next sodium carbonate (5 g) was added, the mixture was stirred 1 h. Then the solution was filtered and solvents were distilled off under reduced pressure (rotary evaporator).

1.10 ppm (t, CH$_3$—C—) 1.51 ppm (m, C—CH$_2$—CH$_2$—), 3.17 ppm (s, CH$_3$-methanesulfonate), 3.49 ppm (bm, —OCH$_2$CH$_2$O—), 4.30 ppm (m, —CH$_2$-methanesulfonate), 4.46 ppm (t, —CH, acetal).

Purity: ~100%.

C. Tetra(ethylene glycol)-α-amino-ω-butyraldehyde, diethyl acetal H$_2$N—(CH$_2$CH$_2$O)$_4$—CH$_2$CH$_2$O—CH$_2$(CH$_2$)$_2$—CH(OCH$_2$CH$_2$)$_2$ A mixture of tetra(ethylene glycol)-α-mesylate-ω-butyraldehyde, diethyl acetal (14.0 g), concentrated ammonium hydroxide (650 ml), and ethyl alcohol (60 ml) was stirred 42 h at room temperature. Next all volatile materials were distilled off under reduced pressure. The crude product was dissolved in 150 ml deionized water and the pH of the solution was adjusted to 12 with 1.0 M NaOH. The product was extracted with dichloromethane (3×100 ml). The extract was dried (MgSO4) and the solvent was distilled off under reduced pressure (rotary evaporator).

Yield 10.6 g. NMR (D$_2$O): 1.09 ppm (t, CH$_3$—C—) 1.56 ppm (m, C—CH$_2$—CH$_2$—), 2.69 ppm (t, CH$_2$—N), 3.56 ppm (bm, —OCH$_2$CH$_2$O—), 4.56 ppm (t, —CH, acetal). Purity: ~100%.

D. Branched PEG2(40.3 KDa)-butyraldehyde, diethyl acetal

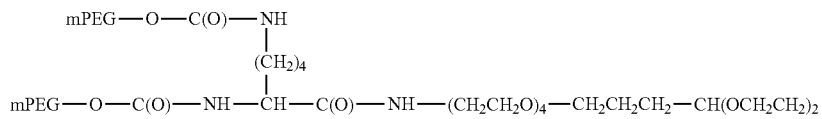

PEG2 (40 KDa)-N-hydroxysuccinimide was prepared from the corresponding PEG2-lysine as described in U.S. Pat. No. 5,932,462 (Harris, J., et al.). The precursor PEG-2 lysine, a branched PEG having an ionizable carboxyl group, was purified by ion exchange chromatography, as also described in U.S. Pat. No. 5,932,462.

To a solution of PEG2 (40 KDa)-N-hydroxysuccinimide (5.0 g, 0.000125 moles) (Shearwater Corporation) in methylene chloride (100 ml), tetra(ethylene glycol)-α-amino-ω-butyraldehyde, diethyl acetal (0.50 g, 0.000148 moles) and triethylamine (0.035 ml) were added and the reaction mixture was stirred overnight at room temperature under an argon atmosphere. The solvent was evaporated to dryness using a rotary evaporator. The crude product was dissolved in methylene chloride and precipitated with isopropyl alcohol. The wet product was dried under reduced pressure. Yield 4.8 g.

NMR (d$_6$-DMSO): 1.10 ppm (t, CH$_3$—C), 1.51 ppm (m, C—CH$_2$—CH$_2$—), 3.24 ppm (s, —OCH$_3$), 3.51 ppm (s, PEG backbone), 4.46 ppm (t, —CH—, acetal). Substitution: ~100%.

E. Branched PEG2(40.3 KDa)-butyraldehyde

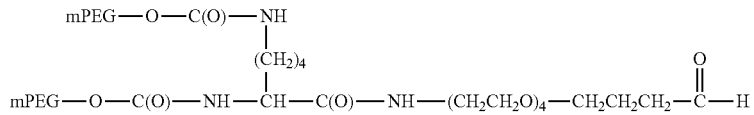

Branched PEG2(40.3 KDa)-butyraldehyde, diethyl acetal (4.8 g) was dissolved in 100 ml water and the pH of the solution was adjusted to 3 with diluted phosphoric acid. The solution was stirred for 3 hours at room temperature, followed by addition of 0.5 M sodium hydroxide sufficient to adjust the pH of the solution to about 7. The product was extracted with methylene chloride, and the extract dried with anhydrous magnesium sulfate. The solvent was distilled off under reduced pressure.

Yield 4.2 g. NMR (d$_6$-DMSO): 1.75 ppm (p, —CH$_1$— CHO—) 2.44 ppm (dt, —CH$_2$—CHO), 3.24 ppm (s, —OCH$_3$), 3.51 ppm (s, PEG backbone), 9.66 ppm (t, —CHO).

Substitution: ~100%.

The above illustrates yet another embodiment of the invention, the preparation of a representative branched PEG alkanal. The above also illustrates an embodiment of the invention wherein the polymer alkanal contains a short oligomeric group, in this case, a tetraethylene glycol interposed between the polymer backbone and the alkanal segment of the molecule. Further, this example illustrates the use of a precursor polymer segment containing an ionizable group such that such polymer segment can be purified by ion exchange chromatography prior to coupling to the alkanal-acetal reagent, thereby effectively removing polymeric impurities early on in the reaction scheme. In this instance, the product formed is absent difunctional polymeric impurities such as those arising from reactions of PEG-diol, or mPEG, or mono-pegylated lysine, or the like, that may have been present in the mPEG2-lysine precursor but were removed by chromatography.

Example 6

Preparation of Polymer-Alkanal Protein Conjugate
Random PEGylation of EPO

Recombinant EPO (produced in *E. coli*, mammalian cells (e.g., CHO cells) or another microbial source) is coupled to mPEG-butryaldehyde 30 kDa (prepared as described in Example 2).

EPO (~2 mg) is dissolved in 1 ml of 50 mM phosphate buffer (pH 7.6) and mPEG(30 kDa)-butyraldehyde is added at 5× the molar EPO concentration. A reducing agent, NaCNBH$_3$ is added and the solution stirred for 24 h at room temperature to couple the PEG-butanal reagent to the protein via an amine linkage.

The reaction mixture is analyzed by SDS-PAGE to determine the degree of PEGylation. Confirmation of the degree of PEGylation, 1-mer, 2 mers, etc. is done by Matrix Assisted Laser Desorption Ionization Time-of-Flight (MALDI-TOF) mass spectrometry. The displayed peaks for native and mono-PEGylated species differ by approximately 30,000 Da. The resulting reaction mixture contains a mixture of native and monopegylated protein. Increasing the ratio of PEG reagent to protein increases the degree of polyPEGylation, that is to say, the formation of 2-mers, 3-mers, etc.

The use of high molecular weight PEG alkanals having molecular weight greater than about 20 kDa favors formation of mono-PEGylated species. Smaller molecular weight PEG alkanals, when coupled to a protein, are more prone to formation of poly-PEGylated species under these conditions.

The above demonstrates random pegylation of an illustrative protein of the invention to yield a distribution of pegylated EPO products. If desired, the reaction mixture can be further separated to isolate the individual isomers as described below.

PEG conjugates having different molecular weights are then separated by gel filtration chromatography. The different PEG conjugates (1-mer, 2-mer, 3-mer, etc.) are fractionated on the basis of their different molecular weights (in this case, varying by approximately 30 kDa). Specifically, the separation is performed by using a serial column system suitable for effective separation of products in the molecular weight range observed, e.g., a Superdex™200 column (Amersham Biosciences). The products are eluted with 10 ml acetate buffer at a flow rate of 1.5 ml/min. The collected fractions (1 ml) are analysed by OD at 280 nm for protein content and also using an iodine test for PEG content (Sims G. E. C., et al., *Anal. Biochem*, 107, 60-63, 1980). Alternatively, the results are visualized by running an SDS PAGE gel, followed by staining with barium iodide. Fractions corresponding to the eluted peaks are collected, concentrated by ultrafiltration using a 10-30 kD cut-off membrane, and lyophilized. This method results in separation/purification of conjugates having the same molecular weights but does not provide separation of conjugates having the same molecular weight but different pegylation sites (i.e., positional isomers).

Separation of positional isomers is carried out by reverse phase chromatography using an RP-HPLC C18 column (Amersham Biosciences or Vydac). This procedure is effective for separating PEG-biomolecule isomers having the same molecular weight (positional isomers). The reverse-phase chromatography is carried out using a RP-HPLC C18 preparative column and eluted with a gradient of water/0.05% TFA (Eluent A) and acetonitrile/0.05% TFA (Eluent B).

Fractions corresponding to the eluted peaks are collected, evaporated to eliminate acetonitrile and TFA, followed by removal of solvent to isolate the individual positional PEG-isomers.

Example 7

Preparation of Polymer-Alkanal Protein Conjugate
N-Terminal PEGylation of EPO

Recombinant EPO (produced in *E. coli*, mammalian cells (such as CHO but not limited to) or another. microbial source) is coupled to mPEG-butryaldehyde, 30 kDa (Example 2).

EPO (~2. mg) is dissolved in 1 ml of 0.1 mM sodium acetate (pH 5) and mPEG(30 kDa)-butyraldehyde (from Example 2) is added at 5× the molar EPO concentration. A reducing agent, NaCNBH₃ is added and the solution is stirred for 24 h at 4° C. to couple the PEG-butanal reagent to the protein via an amine linkage.

The reaction mixture is analyzed by SDS-PAGE to determine the degree of PEGylation. Confirmation of the degree of PEGylation, 1-mer, 2-mers etc. is carried out by Matrix Assisted Laser Desorption Ionization Time-of-Flight (MALDI-TOF) mass spectrometry. The displayed peaks for native and mono-PEGylated species differ by approximately 30,000 Da. The resulting reaction mixture primarily contains a mixture of native and monopegylated protein. The mono-PEGylated species are purified by column chromatography to remove free EPO and higher molecular weight species.

Confirmation of N-terminal PEGylation is carried out by peptide mapping. Increasing the ratio of PEG to protein increases the degree of PEGylation. yielding poly-pegylated protein.

The above demonstrates pegylation of an illustrative protein of the invention to yield a predominantly N-terminal single pegylated protein.

Example 8

N-Terminal PEGylation of GCSF

Recombinant GCSF (produced in *E. coli*, mammalian cells (such as CHO cells) or other microbial source) is coupled to mPEG-butryaldehyde, 30 kDa.

GCSF (~2. mg) is dissolved in 1 ml of 0.1 mM sodium acetate (pH 5) and mPEG(30 kDa)-butyraldehyde (from Example 2) is added at 5× the molar GCSF concentration. The reducing agent, NaCNBH₃ is added and the solution stirred for 24 h at 4° C. to couple the PEG-butanal reagent to the protein via an amine linkage.

The resulting reaction mixture is analyzed by SDS-PAGE to determine the degree of PEGylation. Confirmation of the degree of PEGylation, 1-mer, 2 mers, etc. is carried out by Matrix Assisted Laser Desorption Ionization Time-of-Flight (MALDI-TOF) mass spectrometry. The displayed peaks for native and mono-PEGylated species differ by approximately 30,000 Da. The resulting reaction mixture primarily contains a mixture of native and monopegylated GCSF. The mono-PEGylated species are purified by column chromatography to remove free GCSF and higher molecular weight species. Confirmation of N-terminal PEGylation is conducted by peptide mapping. Increasing the ratio of PEG to protein increases the degree of PEGylation yielding poly-pegylated protein.

Example 9

N-Terminal PEGylation of Interferon α

Recombinant IFN-α (produced in *E. coli*, mammalian cells (such as CHO but not limited to) or other microbial source) is coupled to mPEG-butryaldehyde, 30 kDa.

Interferon-α (~2. mg) is dissolved in 1 ml of 0.1 mM sodium acetate (pH 5) and mPEG(30 kDa)-butyraldehyde (from Example 2) is added at 5× the molar IFN concentration. A reducing agent, NaCNBH₃ is added and the solution stirred for 24 h at 4° C. to couple the PEG-butanal reagent to the protein via an amine linkage.

The reaction mixture is analyzed by SDS-PAGE to determine the degree of PEGylation. Confirmation of the degree of PEGylation, 1-mer, 2 mers etc. is carried out by Matrix Assisted Laser Desorption Ionization Time-of-Flight (MALDI-TOF) mass spectrometry. The displayed peaks for native and mono-PEGylated species differ by approximately 30,000 Da. The resulting reaction mixture primarily contains a mixture of native and monopegylated protein. The Mono-PEGylated species are purified by column chromatography to remove free interferon α and higher molecular weight species. Confirmation of N-terminal PEGylation is conducted by peptide mapping. Increasing the ratio of PEG to protein increases the degree of PEGylation yielding poly-pegylated IFN.

Conjugation of the proteins hGH, IFN-β, and FSH to another illustrative PEG-alkanal, mPEG-2-methyl butyraldehyde, 20 kDa is carried out essentially as described in the examples above.

Example 10

N-Terminal PEGylation of Human Growth Hormone

Recombinant human growth hormone (produced in *E. coli*, mammalian cells (such as CHO but not limited to) or another microbial source) is coupled to mPEG-2-methyl butyraldehyde, 20 kDa.

Human growth hormone (~2 mg) is dissolved in 1 ml of 0.1 mM sodium acetate (pH 5) and mPEG-2-methyl butyraldehyde, 20 kDa is added at 5× the molar hGH concentration. A 5 to 20-fold molar excess of the reducing agent, NaCNBH₃ is added and the solution is stirred for 24 h at 4° C. to couple the PEG-α methylbutanal reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2 mers etc. is carried out by Matrix Assisted Laser Desorption Ionization Time-of-Flight (MALDI-TOF) mass spectrometry. The displayed peaks for native and mono-PEGylated and other species differ by approximately 20,000 Da. The resulting reaction mixture primarily contains a mixture of native and monopegylated protein. The mono-PEGylated species are purified by column chromatography to remove free hGH and higher molecular weight species. Confirmation of N-terminal PEGylation is conducted by peptide mapping. Increasing the ratio of PEG aldehyde to protein increases the degree of PEGylation yielding a population of poly-pegylated hGH.

Example 11

N-Terminal PEGylation of Interferon-β

Recombinant interferon-β (produced in *E. coli*, mammalian cells (such as CHO but not limited to) or another microbial source) is coupled to mPEG-2-methyl butyraldehyde, 20 kDa.

Interferon-β (~2 mg) is dissolved in 1 ml of 0.1 mM sodium acetate (pH 5) and mPEG-2-methyl butyraldehyde, 20 kDa is added at 5× the molar IFN-β concentration. A 5 to 20-fold molar excess of the reducing agent, NaCNBH₃ is added and the solution is stirred for 24 h at 4° C. to couple the PEG-α methylbutanal reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2 mers etc. is carried out by Matrix Assisted Laser Desorption Ionization Time-of-Flight (MALDI-TOF) mass spectrometry. The displayed peaks for native and mono-PEGylated and other species differ by approximately 20,000 Da. The resulting reaction mixture primarily contains a mixture of native and monopegylated protein. The mono-PEGylated species are purified by column chromatography to remove free IFN-β and higher molecular weight species. Confirmation of N-terminal PEGylation is conducted by peptide mapping. Increasing the ratio of PEG aldehyde to protein increases the degree of PEGylation yielding a population of poly-pegylated IFN-β.

Example 12

N-Terminal PEGylation of FSH

Recombinant follicle stimulating hormone (produced in *E. coli*, mammalian cells (such as CHO but not limited to) or another microbial source) is coupled to mPEG-2-methyl butyraldehyde, 20 kDa.

Follicle stimulating hormone, FSH (~2 mg) is dissolved in 1 ml of 0.1 mM sodium acetate (pH 5) and mPEG-2-methyl butyraldehyde, 20 kDa is added at 5× the molar FSH concentration. A 5 to 20-fold molar excess of the reducing agent, $NaCNBH_3$, is added and the solution is stirred for 24 h at 4° C. to couple the PEG-α methylbutanal reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2 mers etc. is carried out by Matrix Assisted Laser Desorption Ionization Time-of-Flight (MALDI-TOF) mass spectrometry. The displayed peaks for native and mono-PEGylated and other species differ by approximately 20,000 Da. The resulting reaction mixture primarily contains a mixture of native and monopegylated protein. The mono-PEGylated species are purified by column chromatography to remove free FSH and higher molecular weight species. Confirmation of N-terminal PEGylation is conducted by peptide mapping. Increasing the ratio of PEG aldehyde to protein increases the degree of PEGylation yielding a population of poly-pegylated FSH.

Example 13

N-Terminal PEGylation of Human Growth Hormone

Recombinant hGH (produced in *E. coli*, mammalian cells (such as CHO but not limited to) or another microbial source) is covalently attached to branched PEG2 (40.3 KDa)-butyraldehyde (Example 5E).

Human growth hormone (~2 mg) is dissolved in 1 ml of 0.1 mM sodium acetate (pH 5) and branched PEG2 (40.3 KDa)-butyraldehyde is added at 5× the molar hGH concentration. A 5 to 20-fold molar excess of the reducing agent, $NaCNBH_3$, is added and the solution is stirred for 24 h at 4° C. to couple the branched PEG2 (40.3 KDa)-butyraldehyde reagent to the protein via an amine linkage.

Progress of the reaction is analyzed by SDS-PAGE or MALDI-TOF mass spectrometry to determine the extent of PEGylation. Confirmation of the degree of PEGylation, 1-mer, 2 mers (if any) etc., is carried out by Matrix Assisted Laser Desorption Ionization Time-of-Flight (MALDI-TOF) mass spectrometry. The displayed peaks for native and mono-PEGylated and other species differ by approximately 40,000 Da. The resulting reaction mixture primarily contains a mixture of native and monopegylated protein, in particular due to the size and geometry of the branched PEG alkanal reagent. The mono-PEGylated species are purified by column chromatography to remove free hGH and higher molecular weight species. Confirmation of N-terminal PEGylation is conducted by peptide mapping.

Example 14

PEGylation of Amphotericin B

The amino group of a small molecule, amphotericin B, is modified by attachment of a polymer alkanal.

To a solution of amphotericin B.HCl in deionized water is added a 2-fold molar excess of $mPEG_{2k}$-butyraldehyde (Example 1) dissolved in 0.1 M phosphate buffer at pH 6.5. To this mixture is added a solution of $NaCNBH_3$ (at a 1.5 to 10-fold molar excess) in phosphate buffer at pH 6.5, and the resulting solution is stirred at room temperature overnight under an argon atmosphere. Aliquots of the reaction mixture are withdrawn at various time intervals to monitor the progress of the reaction by $^1H$ NMR. Upon completion, the reaction mixture is further diluted by addition of water, and NaCl is added to achieve saturation. The product is then extracted with dichloromethane, and the combined organic extracts are dried over anhydrous sodium sulfate, filtered to remove drying agent, and the solvent evaporated by rotary evaporation. The product is then precipitated by addition of diethyl ether, and dried under vacuum overnight. The recovered product is analyzed by gel permeation chromatography to determine the extent of conjugation.

The crude product is purified by cation exchange chromatography using Poros 50 HS cation exchange resin (PerSeptive BioSystems, Framingham, Mass.). Following washing of the column with deionized water, the product is eluted with 1N NaCl solution. The conjugate containing extracts are combined, and the product is extracted with dichloromethane. The organic solution is dried over anhydrous sodium sulfate, filtered, and the solvent evaporated by rotary evaporation. The purified conjugate is purified by addition of diethyl ether.

If necessary, the product is further purified by reverse phase HPLC chromatography using a Betasil C18 column, Keystone Scientific).

Example 15

Preparation of PEG(3500 DA)-α-Hydroxy-ω-Butyraldehyde by Anionic Ring Opening Polymerization of Ethylene Oxide Directly onto an Anionic Acetal Precursor In this example, an acetal precursor having a site suitable for initiating ring-opening polymerization with ethylene oxide is prepared by reacting 4-chloro-butyraldehyde• diethyl acetal with the di-alcohol, ethylene glycol. In this way, a halo-acetal is converted to a hydroxyl-terminated acetal. The hydroxyl group, when converted to the corresponding alkoxide anion, provides a site for initiating polymerization of ethylene oxide (EO), to thereby form a polymer alkanal precursor. The polymer alkanal precursor (acetal), upon hydrolysis, is converted to the desired polymer alkanal.

A generalized scheme for this synthetic approach for preparing a polymer alkanal of the invention is shown in FIG. 1.

A. Preparation of 2-(4,4-diethoxy-butoxy)ethanol (Compound 15A)

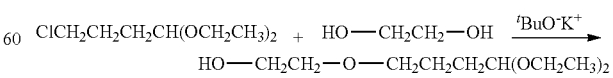

A mixture of anhydrous ethylene glycol (120 g, 1.93 moles), a 1.0M solution of potassium tert-butoxide in tert-butanol (70 ml, 0.07 moles), and 4-chlorobutyraldehyde diethyl acetal (11 g, 0.061 moles) is stirred overnight at 100°

C. under an argon atmosphere. After cooling to room temperature, the reaction mixture is added to 600 ml distilled water. The product is extracted with dichloromethane (150, 125, and 125 ml). The combined extracts are then dried with anhydrous magnesium sulfate and the solvent is distilled off under reduced pressure. Next the product is subjected to vacuum distillation (kugelrohr, t=90-110° C., 0.10 mm Hg). Yield 5.5 g.

NMR (d$_6$-DMSO): 1.11 ppm (t, 6H), 1.53 ppm (m, —CH$_2$CH, 2H), 1.64 ppm (m, —CH$_2$CH$_2$CH, 2H), 3.37 ppm (t, —O—CH$_2$CH$_2$CH$_2$CH, 2H), 3.53 ppm (t, HO—CH$_2$CH$_2$O—, 2H), 3.62 ppm (q, —CH$_2$CH$_3$, 4H), 3.70 ppm (t, HO—CH$_2$—, 2H), 4.38 ppm (t, —CH acetal, 1H), 4.54 ppm (t, 1H, —OH).

B. Preparation of PEG(3,500 Da)-α-hydroxy-ω-butyraldehyde diethyl acetal

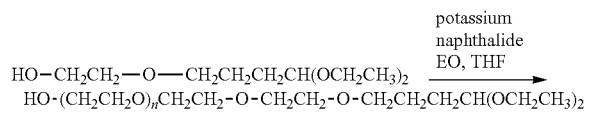

Compound 15A (0.51 g, 0.00247 moles), THF 200 ml, and potassium naphthalide (0.3 mol/L-tetrahydrofuran solution, 20 ml, 0.006 moles) are added to a glass reactor and stirred for 3 minutes in an argon atmosphere. Ethylene oxide (8.8 g 0.20 moles) is added to this solution and the reaction mixture is stirred for 44 h at room temperature. Next the mixture is purged with argon and 0.1M phosphate buffer (pH=8, 100 ml) is added. The THF layer is separated and discarded. Naphthalene is removed from the solution by ethyl ether extraction. The product is extracted from the residue with dichloromethane (3×50 ml). The extract is dried with anhydrous sodium sulfate and concentrated to about 30 ml. Next ethyl ether (250 ml) is added and the mixture is stirred 15 min at 0° C. The precipitated product is filtered off and dried under reduced pressure.

Yield 7.2 g.

NMR (d$_6$-DMSO): 1.09 ppm (t, CH$_3$—, 3H) 1.52 ppm (m, C—CH$_2$—CH$_2$—, 4H), 3.51 ppm (s, polymer backbone), 4.46 ppm (t, —CH, acetal, 1H), 4.57 ppm (t —OH, 1H).

C. PEG(3,500 Da)-α-hydroxy-ω-butyraldehyde

A mixture of PEG(3,500)-□-hydroxy-□-butyraldehyde diethyl acetal (1.0 g), deionized water (20 ml), and 5% phosphoric acid to adjust the pH to 3.0 is stirred for 3 hours at room temperature. Next, sodium chloride (1.0 g) is added and the pH is adjusted to 6.8 with 0.1 M sodium hydroxide. The product is extracted with dichloromethane (3×20 ml). The extract is dried with anhydrous magnesium sulfate and the solvent is distilled off. The wet product is dried under reduced pressure. Yield: 0.82 g.

NMR (d6-DMSO): 1.75 ppm (p, —CH2—CH2-CHO—) 2.44 ppm (dt, —CH2—CHO), 3.51 ppm (s, polymer backbone), 4.57 ppm (t, —OH), 9.66 ppm (t, —CHO).

Example 16

Preparation of Methoxy-PEG(3500 DA) Butyraldehyde

This example demonstrates the preparation of an illustrative end-capped PEG-alkanal from a PEG α-hydroxy-ω-alkanal acetal.

A. mPEG(3,500 Da)-butyraldehyde diethyl acetal

A mixture of PEG(3,500 Da)-α-hydroxy-ω-butyraldehyde diethyl acetal (3.5 g, 0.001 moles), toluene (50 ml), 1.0M solution of potassium tert-butoxide in tert-butanol (5 ml, 0.005 moles) and methyl p-toluene sulfonate (0.75 g, 0.004 moles) is stirred overnight at 45° C. Next, the solvents are distilled off under reduced pressure (rotoevaporator). The crude product is dissolved in dichloromethane and added to cold ethyl ether. The precipitated product is filtered off and dried under reduced pressure. Yield: 3.1 g.

NMR (d$_6$-DMSO): 1.09 ppm (t, CH$_3$—, 3H) 1.52 ppm (m, C—CH$_2$—CH$_2$—, 4H), 3.24 ppm (s, CH$_3$O—, 3H), 3.51 ppm (s, polymer backbone), 4.46 ppm (t, —CH, acetal, 1H).

B. mPEG(3,500 Da)-butyraldehyde

A mixture of mPEG(3,500)-butyraldehyde diethyl acetal (1.0 g), deionized water (20 mL), and 5% phosphoric acid to adjust the pH to 3.0 is stirred for 3 hours at room temperature. Next, sodium chloride (1.0 g) is added and the pH is adjusted to 6.8 with 0.1 M sodium hydroxide. The product is extracted with dichloromethane (3×20 ml). The extract is dried with anhydrous magnesium sulfate and the solvent is distilled off. The wet product is dried under reduced pressure. Yield: 0.85 g.

NMR (d$_6$-DMSO): 1.75 ppm (p, —CH$_2$—CH$_2$—CHO—, 2H) 2.44 ppm (dt, —CH$_2$—CHO, 2H), 3.24 ppm (s, —OCH$_3$, 3H), 3.51 ppm (s, polymer backbone), 9.66 ppm (t, —CHO, 1H).

Example 17

Preparation of Methoxy-PEG(2 KDa) 2-Methylbutyraldehyde

This example describes the synthesis of an illustrative polymer 2-alkylsubstituted alkanal of the invention. This polymer, rather than possessing a straight alkylene chain separating the aldehyde carbon from the linker, possesses a methyl substituent in the C-2 position.

OVERVIEW: The protected acetal reagent, 17-A, was prepared from a commercially available starting material, 2-methyl-4-chlorobutanoate, by first reducing the butanoate carbon to the corresponding alcohol, followed by oxidation to the butyraldehyde. The butyraldehyde was then protected as the corresponding acetal to provide a protected acetal reagent for coupling to PEG. Following coupling to PEG, the resulting polymer acetal was hydrolyzed in acid to provide the desired polymer alkanal.

A. Preparation of 4-chloro-2-methylbutyraldehyde diethyl acetal

Preparation of 4-chloro-2-methylbutanol-1

A solution of 2-methyl 4-chlorobutanoate (TCI America) (22.0 g, 0146 moles) in ethyl ether (80 ml) was added dropwise during 30 min to a stirred solution of lithium aluminum hydride (4.55 g, 0.12 moles) in ethyl ether (360 ml) at 0° C. under argon atmosphere. Next methanol (12 ml) was added dropwise over a period of 30 min and then ice-cold 2N HCl (420 ml) was added dropwise over a 20 minute period. The reaction mixture was transferred to a separatory funnel and the ether layer, containing 4-chloro-2-methylbutanol-1, was separated. Additional product was extracted from the water layer with ethyl ether (3×200 ml). The ether extracts were combined, dried with anhydrous magnesium sulfate, and the solvent was distilled under reduced pressure. Yield 18.6 g.

NMR (d$_6$-DMSO): 0.84 ppm (d, —CH$_3$, 3H), 1.50 ppm (m, —CH$_2$CH$_2$Cl, 1H), 1.68 ppm (m, —CH—, 1H), 1.82 ppm (m, —CH$_2$CH$_2$Cl, 1H) 3.26 ppm (t, —CH$_2$OH, 2H), 3.66 ppm (m, —CH$_2$Cl, 2H), 4.50 ppm (t, —OH, 1H).

4-Chloro-2-methylbutyraldehyde

Pyridinium chlorochromate (23.6 g, 0.110 g) was added gradually to a stirred solution of 4-chloro-2-methylbutanol-1

(8.80 g, 0.078 moles) in anhydrous dichloromethane (470 ml). The mixture was stirred overnight at room temperature under an argon atmosphere. Dry ether (820 ml) was added; the mixture was stirred for 20 minutes, and then was filtered to remove excess of oxidizing agent. The solution was then filtered through a column filled with 400 g of Florisil, and the solvents were distilled off under reduced pressure. Yield 6.0 g.

NMR ($d_6$-DMSO): 1.06 ppm (d, —$CH_3$, 3H), 1.74 ppm (m, —$CH_2CH_2Cl$, 1H), 2.14 ppm (m, —$CH_2CH_2Cl$, 1H), 2.56 ppm (m, —CH, 1H), 3.69 ppm (m, —$CH_2Cl$, 2H), 9.60 ppm (t, —CHO, 1H).

4-Chloro-2-methylbutyraldehyde diethyl acetal

A mixture of 4-chloro-2-methylbutyraldehyde (4.8 g, 0.040 moles), triethyl orthoformate (6.48 g, 0.044 moles), ethyl alcohol (3.0 g), and p-toluenesulfonic acid monohydrate (0.0144 g, 0.000757 moles) was stirred at 45° C. overnight under an argon atmosphere. Next, after cooling to room temperature, $Na_2CO_3$ (0.40 g) was added and the mixture was stirred for 15 min. The reaction mixture was filtered and ethyl alcohol and residual triethyl orthoformate were distilled off under reduced pressure. The residue was subjected to fractional vacuum distillation giving 3.2 g of pure 4-chloro-2-methylbutyraldehyde diethyl acetal.

NMR ($d_6$-DMSO): 0.85 ppm (d, —$CH_3$, 3H) 1.13 ppm (m, —$CH_3$, 6H), 1.52 ppm (m, —CH—, 1H), 1.87 ppm (m, —$CH_2CH_2Cl$, 2H), 3.35-3.75 ppm (bm, —$OCH_2CH_3$, 4H, and —$CH_2Cl$, 2H), 4.22 ppm (d, —CH acetal, 1H).

B. mPEG (2K Da)-2-Methylbutyraldehyde, diethyl acetal

A solution of mPEG (2K Da) (2.0 g, 0.001 moles) in toluene (30 ml) was azeotropically dried by distilling off toluene under reduced pressure. The dried mPEG 2K was dissolved in anhydrous toluene (15 ml) and 1.0 M solution of potassium tert-butoxide in tert-butanol (4.0 ml, 0.004 moles) and 4-chloro-2-methylbutyraldehyde diethyl acetal from A above (0.5 g, 0.00277 moles) were added. Next, lithium bromide (0.05 g) was added and the mixture was stirred at 100° C. overnight under an argon atmosphere. After cooling to room temperature, the mixture was filtered and added to 150 ml ethyl ether at 0-5° C. The precipitated product was filtered off and dried under reduced pressure. Yield: 1.5 g.

NMR ($d_6$-DMSO): 0.83 ppm (d, —$CH_3$, 3H) 1.10 ppm (m, —$CH_3O$, 6H), 1.24 ppm (m, —CH—, 1H), 1.72 ppm (m, PEG-O—$CH_2$—$CH_2$—, 2H), 3.24 ppm (s, —$OCH_3$, 3H), 3.51 ppm (s, polymer backbone), 4.18 ppm (d, —CH acetal, 1H).

Substitution: ~100%.

C. mPEG (2K Da)-2-Methylbutyraldehyde

A mixture containing mPEG (2K Da)-2-methylbutyraldehyde, diethyl acetal from B above (1.0 g), deionized water (20 ml), and 5% phosphoric acid to adjust the pH to 3.0 was stirred for 3 hours at room temperature. Next, sodium chloride (1.0 g) was added and the pH was adjusted to 6.8 with 0.1 M sodium hydroxide. The product was extracted with dichloromethane (3×20 ml). The extract was dried with anhydrous magnesium sulfate and the solvent was distilled off under reduced pressure. Yield: 0.83 g.

NMR ($d_6$-DMSO): 1.01 ppm (d, —$CH_3$, 3H) 1.56 ppm (m, —CH, 1H), 1.90 ppm (m, PEG-O—$CH_2$—$CH_2$—, 1H), 2.45 ppm (m, PEG-O—$CH_2$—$CH_2$—, 1H), 3.24 ppm (s, —$OCH_3$, 3H), 3.51 ppm (s, polymer backbone), 9.56 ppm (d, —CH aldehyde, 1H).

Substitution: ~100%.

What is claimed is:

1. A method of forming a water-soluble polymer alkanal, said method comprising the steps of:
   reacting a water soluble polymer comprising at least one reactive group, Y, with a protected alkanal reagent comprising from about 2 to 20 carbon atoms and a reactive group, K, suitable for displacement by or alternatively, reaction with Y, under conditions effective to form a water soluble polymer alkanal in protected form.

2. The method of claim 1, further comprising hydrolyzing the water soluble polymer alkanal in protected form under acidic conditions to thereby form the corresponding water-soluble polymer alkanal.

3. The method of claim 2, wherein the protected alkanal reagent comprises 4 or more carbon atoms.

4. The method of claim 2, wherein the hydrolyzing is carried out at a pH of no lower than about 3.

5. The method of claim 1, wherein the water-soluble polymer comprises the structure, POLY-Y, and the protected alkanal reagent comprises the structure,

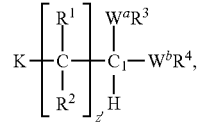

XI-D wherein:
z' is an integer from 1 to about 21;
$R^1$, in each occurrence, is independently H or an organic radical selected from the group consisting of alkyl, substituted alkyl, alkenyl, substituted alkenyl, alkynyl, substituted alkynyl, aryl, and substituted aryl;
$R^2$, in each occurrence, is independently H or an organic radical selected from the group consisting of alkyl, substituted alkyl, alkenyl, substituted alkenyl, alkynyl, substituted alkynyl, aryl, and substituted aryl,
$W^a$ and $W^b$ are each independently O or S, and
$R^3$ and $R^4$ are each independently H or an organic radical selected from the group consisting of methyl, ethyl, isopropyl, benzyl, 1,1,1-trichoroethyl, and nitrobenzyl, or when taken together, are —$(CH_2)_2$— or —$(CH_2)_3$—, forming a 5 or 6 membered ring when considered together with $W^a$, $C_1$, and $W^b$.

6. The method of claim 5, wherein POLY is selected from the group consisting of poly(alkylene oxide), poly(vinyl pyrrolidone), poly(vinyl alcohol), polyoxazoline, poly(acryloylmorpholine), and poly(oxyethylated polyol).

7. The method of claim 6, wherein POLY is a poly(ethylene glycol).

8. The method of claim 7, wherein the poly(ethylene glycol) is terminally capped with an end-capping moiety.

9. The method of claim 8, wherein:
POLY-Y comprises the structure Z—$(CH_2CH_2O)_n$H, wherein n is from about 10 to about 4000, and Z is selected from the group consisting of —$OCH_3$, —$OCH_2CH_3$, —$OCH_2(C_6H_5)$,
and K is selected from the group consisting of:

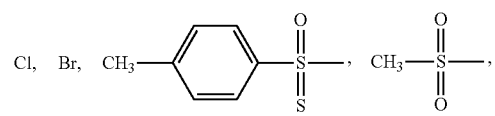

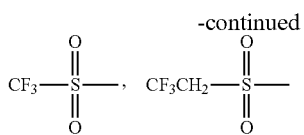

wherein:
R¹ and R² are each independently H or lower alkyl, and Wᵃ and Wᵇ are each O.

10. The method of claim 9, wherein z' ranges from 4 to about 8.

11. The method of claim 9, wherein R¹ and R² are both H in each occurrence.

12. The method of claim 9, wherein said a water-soluble polymer alkanal in protected form is formed in greater than about 85% yield.

13. The method of claim 9, further comprising hydrolyzing said water soluble polymer alkanal in protected form under acidic conditions to thereby form the corresponding water soluble polymer alkanal in a reaction mixture.

14. The method of claim 12, further comprising the step of isolating the alkanal from the reaction mixture.

15. The method of claim 14, wherein said isolating comprises:
raising the pH of the reaction mixture to from about 6.0 to 7.5,
extracting the alkanal into an organic solvent, and
removing the solvent.

16. The method of claim 15, wherein said isolated alkanal is absent detectable amounts of Z—(CH₂CH₂O)ₙH and retro-Michael type reaction products.

17. The method of claim 16, wherein said isolated alkanal has a purity of at least about 95%, based upon polymeric contaminants.

18. The method of claim 7, wherein:
POLY-Y comprises the structure HO—(CH₂CH₂O)ₙH, wherein n is from about 10 to about 4000,
and K is selected from the group consisting of:

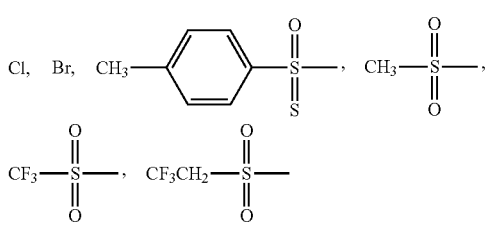

wherein:
R¹ and R² are each independently H or lower alkyl, and
Wᵃ and Wᵇ are each O, to form an alkanal in protected form having the structure:

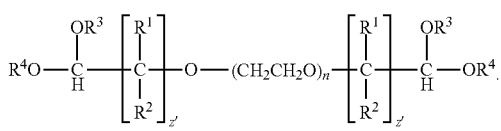

XII

19. The method of claim 7, wherein:
POLY-Y comprises the structure Z—(CH₂CH₂O)ₙH, wherein n is from about 10 to about 4000, and Z is protected hydroxyl,
and K is selected from the group consisting of:

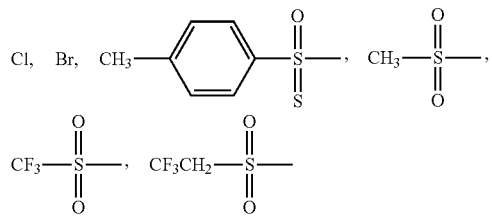

wherein:
R¹ and R² are each independently H or lower alkyl, and
Wᵃ and Wᵇ are each O.

20. The method of claim 18, further comprising after said reacting step, deprotecting said protected hydroxyl to form

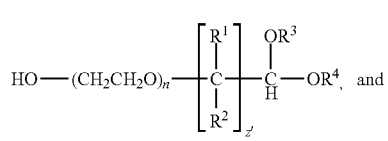

XI-E converting said terminal —OH on the poly(ethylene glycol) to a functional group other than hydroxyl.

21. The method of claim 19, wherein said functional group is selected from the group consisting of amino, ester, carbonate, aldehyde, alkenyl, acrylate, methacrylate, acrylamide, sulfone, thiol, carboxylic acid, isocyanate, isothiocyanate, maleimide, vinylsulfone, dithiopyridine, vinylpyridine, iodoacetamide, and silane.

22. The method of claim 7, wherein Y in said POLY-Y is an ionizable group or is a derivative of an ionizable group.

23. The method of claim 21, wherein Y is selected from the group consisting of carboxylic acid, active ester, and amine.

24. The method of claim 22, wherein said POLY-Y has been chromatographically purified prior to use in said reacting step.

25. The method of claim 23, wherein said POLY-Y has been purified by ion exchange chromatography.

26. The method of claim 23, wherein said POLY-Y for use in said reacting step is essentially absent detectable amounts of polymeric impurities.

27. The method of claim 23, wherein said POLY-Y for use in said reacting step is end-capped, and is essentially absent detectable amounts of PEG-diol or difunctional PEG impurities.

28. The method of claim 13, further comprising the step of conjugating said water soluble polymer alkanal with a biologically active agent comprising an amino group.

* * * * *